US010603443B2

(12) United States Patent
Schenker et al.

(10) Patent No.: US 10,603,443 B2
(45) Date of Patent: Mar. 31, 2020

(54) DRIVING AND DOSING DEVICE FOR AN INJECTION DEVICE WITH A PRETENSIONED DRIVING SPRING

(71) Applicant: TecPharma Licensing AG, Burgdorf (CH)

(72) Inventors: Susanne Schenker, Langenthal (CH); Ursina Streit, Schonbuhl (CH); Patrick Hostettler, Hasle (CH)

(73) Assignee: TecPharma Licensing AG, Burgdorf (CH)

( * ) Notice: Subject to any disclaimer, the term of this patent is extended or adjusted under 35 U.S.C. 154(b) by 12 days.

(21) Appl. No.: 15/173,321

(22) Filed: Jun. 3, 2016

(65) Prior Publication Data

US 2016/0279340 A1    Sep. 29, 2016

Related U.S. Application Data

(63) Continuation of application No. PCT/CH2014/000161, filed on Nov. 6, 2014.

(30) Foreign Application Priority Data

Dec. 5, 2013 (EP) .................................... 13195948

(51) Int. Cl.
*A61M 5/315* (2006.01)
*A61M 5/20* (2006.01)
*A61M 5/31* (2006.01)

(52) U.S. Cl.
CPC .......... *A61M 5/31585* (2013.01); *A61M 5/20* (2013.01); *A61M 5/31553* (2013.01); *A61M 5/31583* (2013.01); *A61M 2005/3126* (2013.01)

(58) Field of Classification Search
CPC .............. A61M 5/2033; A61M 5/3155; A61M 5/31556; A61M 5/31585; A61M 5/31583;
(Continued)

(56) References Cited

U.S. PATENT DOCUMENTS 5,104,380 A    4/1992    Homan et al.
2002/0052578 A1*    5/2002    Moller .................... A61M 5/24
                                                                    604/208
(Continued)

FOREIGN PATENT DOCUMENTS

EP    2644217 A1    10/2013
WO    2008/031237 A1    3/2008
(Continued)

OTHER PUBLICATIONS

PCT International Search Report for International Application No. PCT/CH2014/000161 dated Dec. 18, 2014.
(Continued)

*Primary Examiner* — Kevin C Sirmons
*Assistant Examiner* — Tezita Z Watts
(74) *Attorney, Agent, or Firm* — Dorsey & Whitney LLP

(57) ABSTRACT

A driving and dosing device for an injection device for discharging a liquid product includes a housing, a rotatable dose adjustment member for adjusting a product dose to be discharged, a driven member received in the housing, a driving member rotatable relative to the housing and which, during the discharge of product, is coupled to the driven member such that a rotation of the driving member has the effect that the driven member is moved in the distal direction relative to the housing, a pretensioned driving spring which is switched between the dose adjustment member and the driving member during the adjustment of the product dose, wherein the dose adjustment member, during the adjustment of the product dose, is coupled in a rotationally fixed manner (Continued)

to the driving member, such that a rotation of the driving member relative to the dosing member is prevented.

24 Claims, 10 Drawing Sheets

(58) Field of Classification Search
CPC ........ A61M 5/31573; A61M 2205/202; A61M 2205/3125
See application file for complete search history.

(56) References Cited

U.S. PATENT DOCUMENTS

| | | | |
|---|---|---|---|
| 2009/0318865 A1* | 12/2009 | Moller | A61M 5/31553 604/135 |
| 2010/0168677 A1* | 7/2010 | Gabriel | A61M 5/31551 604/189 |
| 2011/0034878 A1* | 2/2011 | Radmer | A61M 5/315 604/192 |
| 2011/0125100 A1* | 5/2011 | Schwirtz | A61M 5/002 604/198 |
| 2012/0197207 A1* | 8/2012 | Stefanski | A61M 5/20 604/189 |

FOREIGN PATENT DOCUMENTS

| | | |
|---|---|---|
| WO | 2009/105910 A1 | 9/2009 |
| WO | 2010/105376 A1 | 9/2010 |
| WO | 2013/119132 A1 | 8/2013 |

OTHER PUBLICATIONS

PCT International Preliminary Report on Patentability for International Application No. PCT/CH2014/000161 dated Jun. 7, 2016.

\* cited by examiner

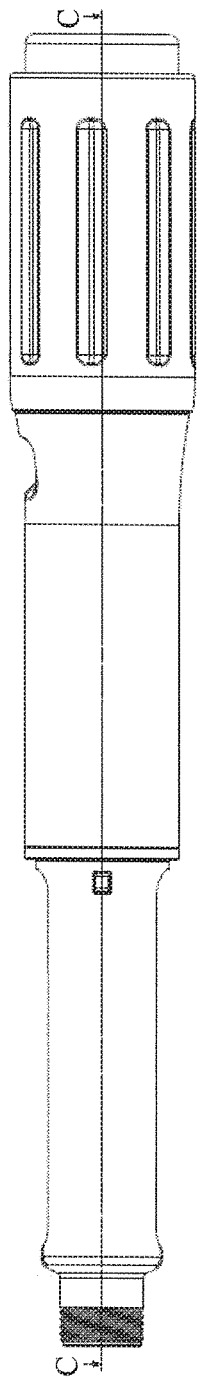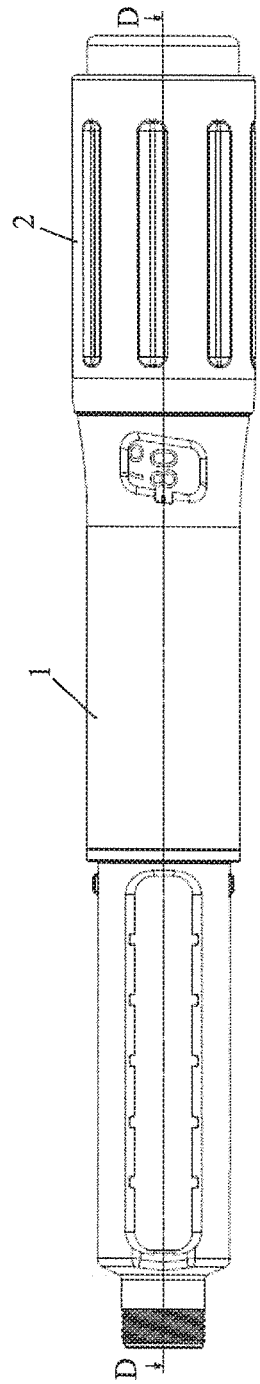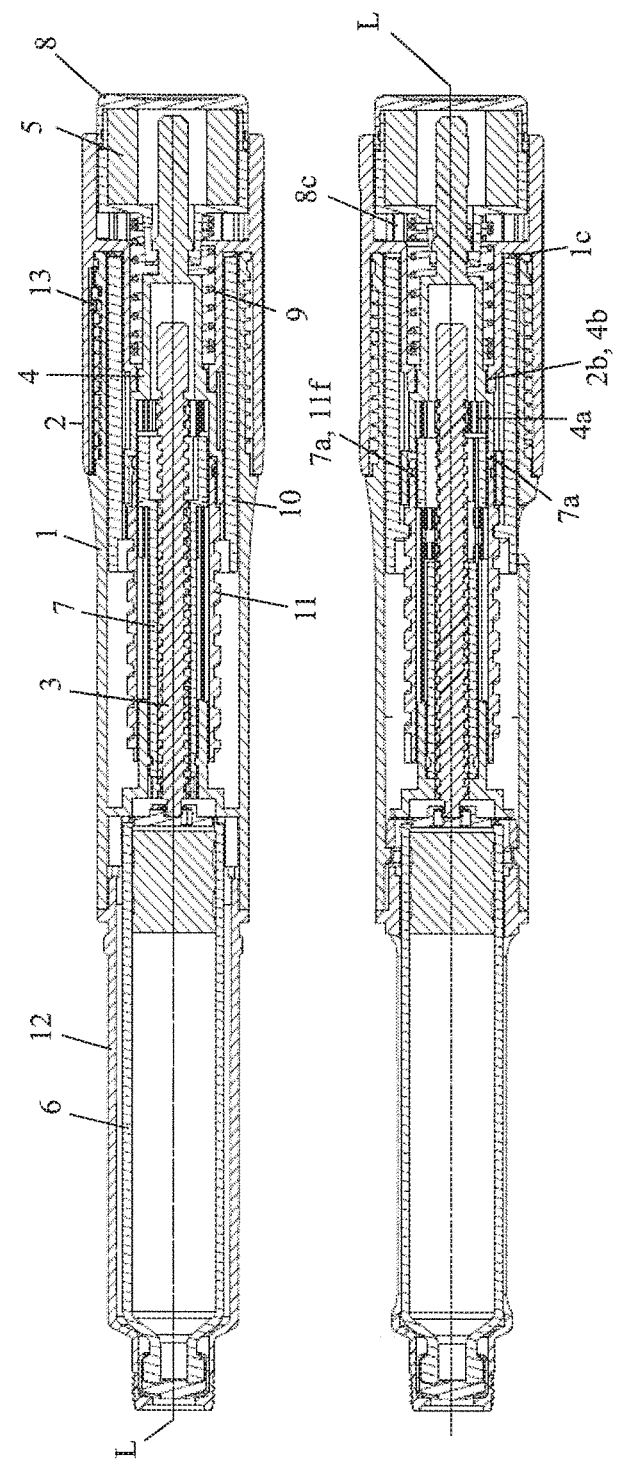
Figure 4A
Figure 4B
Figure 4C
Figure 4D

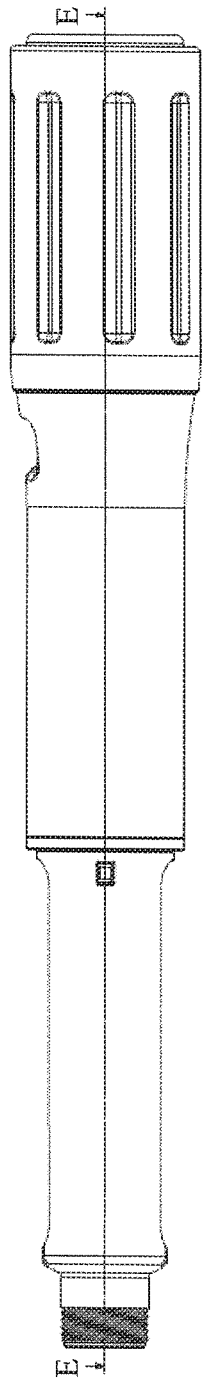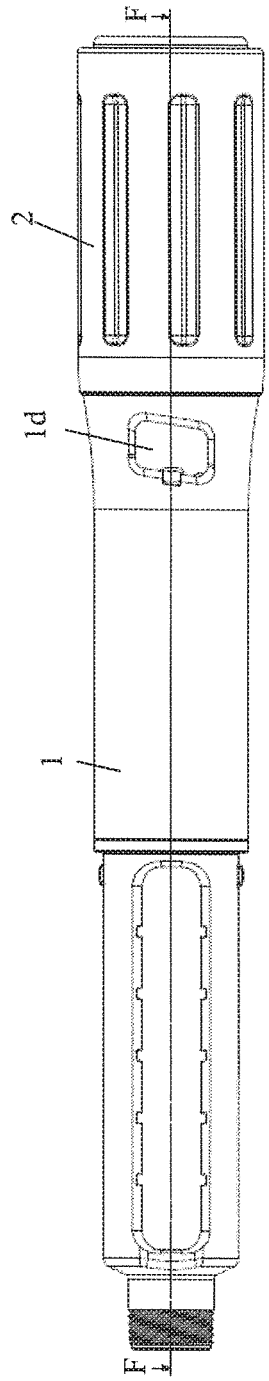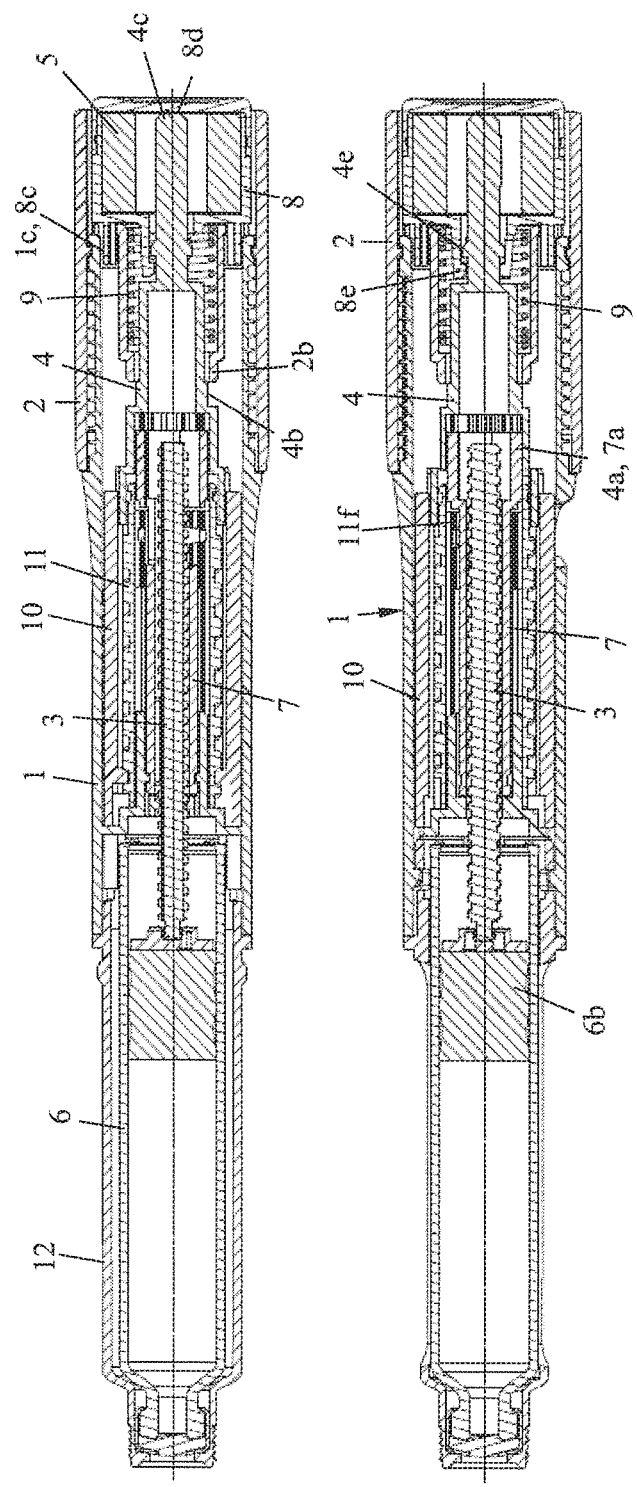
Figure 5A
Figure 5B
Figure 5C
Figure 5D

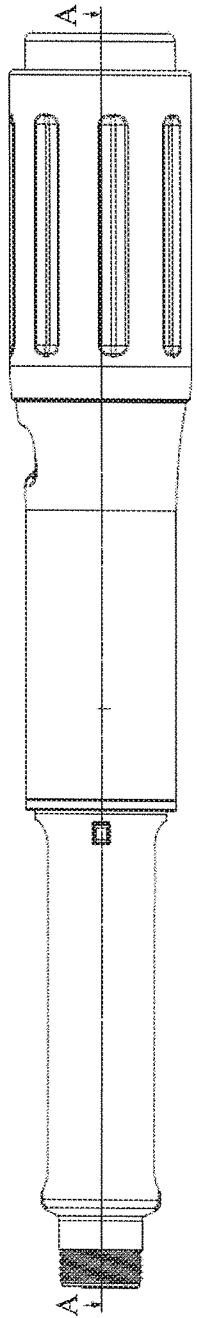
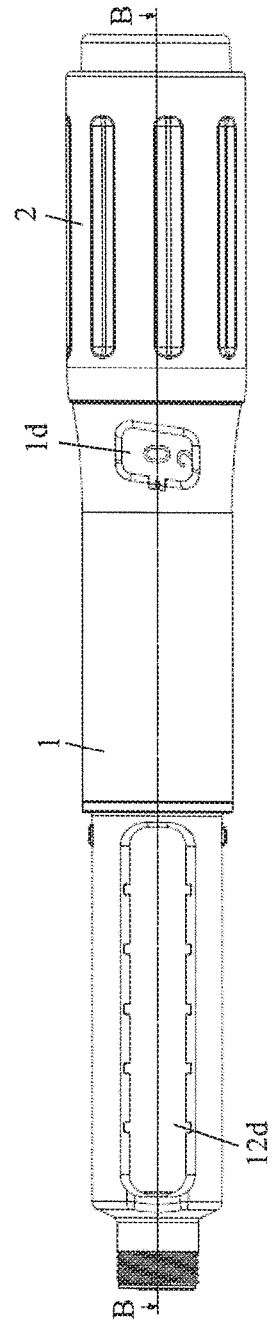
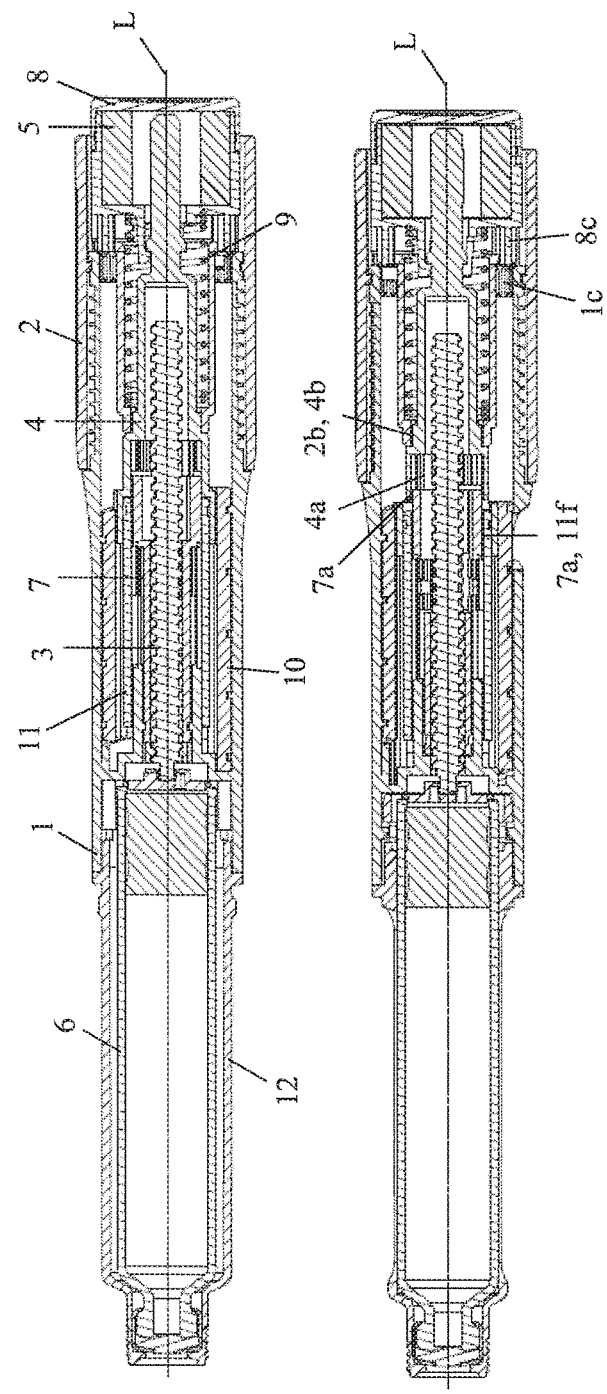
Figure 9A
Figure 9B
Figure 9C
Figure 9D

DRIVING AND DOSING DEVICE FOR AN INJECTION DEVICE WITH A PRETENSIONED DRIVING SPRING

CROSS-REFERENCE TO RELATED APPLICATIONS

This application is a Continuation of International Patent Application No. PCT/CH2014/000161 filed Nov. 6, 2014, which claims priority to European Patent Application No. 13195948.8 filed Dec. 5, 2013, the entire contents of each are incorporated herein by reference for any and all purposes.

BACKGROUND

The invention concerns a drive and dosing device for an injection device for administration or discharge of a liquid product, in particular a medication, for example insulin for diabetes treatment. In particular, the invention also concerns an injection device that has such a drive and dosing device.

The term "medication" here comprises any flowable medicinal formulation that is suitable for controlled administration through a means like a cannula or hollow needle, for example a liquid, a solution, a gel, or a fine suspension that contains one or more medicinal agents. "Medication" can be a composition having a single active agent or a premixed or co-formulated composition having a plurality of active agents in a single container. "Medication" comprises drugs like peptides (for example, insulins, insulin-containing medications, GLP-1-containing as well as derivative or analogous preparations), proteins and hormones, biologically obtained or active agents, agents based on hormones or genes, nutrient formulations, enzymes, and other substances both in solid (suspended) or liquid form, and also polysaccharides, vaccines, DNA or RNA, or oligonucleotides, antibodies or parts of antibodies, as well as suitable basic agents, auxiliary substances, and vehicles.

An injection device having a dose display drum and a drive spring is known from the prior art, for example WO 2008/031237 A1. The drive spring is a clock spring, which is wound in a spiral from a strip material. In the selection of the desired product dose, the spring is tensioned with a rotary motion. To discharge the dose, a piston rod of the device is coupled to the spring by actuation of an actuation button at the proximal end of the device, whereby the spring can transmit the energy stored in it to the piston rod, due to which the piston rod is moved in the discharge direction. To select a new dose, the spring is again tensioned by rotating the dosing button. This is repeated until the product container is empty.

An injection device with a coil spring is known from U.S. Pat. No. 5,104,380 A, the coil spring being likewise tensioned by rotation during dose selection, so that the coil spring can be called a torsion spring. The spring, which is tensioned before each product discharge by rotation of a rotatable button, transmits its energy to the piston rod in order to drive it.

EP 2 644 217 A1 describes an injection device with a dose display and a spring drive, where a spring that has been pretensioned in the delivered state of the device and that acts between an advancing member and an abutment has been pretensioned with enough energy that it can discharge the maximum amount of product that can be discharged from the product container in a plurality of individual discharges.

SUMMARY

The invention is based on the problem of specifying a drive and dosing device for an injection device that allows simple use of the device for the user, in particular simple dose selection, and nevertheless enables a compact construction.

The problem is solved through the features of the claims, which additionally include advantageous developments, and these solutions and developments are further provided in the description and the figures.

The invention originates from a drive and dosing device for an injection device for administration of a liquid medication or product. The drive and dosing device has a housing. The housing is preferably made sleeve-shaped and/or elongated. The housing can, for example, extend along its lengthwise axis (e.g., longitudinal axis).

The housing can optionally accommodate a product container or itself form the product container. The housing can be made in one piece or have a plurality of parts. For example, the housing can form a proximal housing part, which essentially forms the drive and dosing device, i.e., comprises or has a drive and dosing mechanism. The housing can additionally have a product container holder, which accommodates the product container, for example a cartridge, and is connected to the housing or the proximal housing part. The connection can be such that the product container holder and the housing or the proximal housing part cannot be separated after being connected, i.e., they can only be separated by destroying the connecting elements. Such a solution is advantageous in particular in the case of one-way, disposable injection devices, which are discarded in their entirety after the product contained in the product container has been completely discharged. Alternatively, the product container holder can also be separably affixed to the housing, so that it is optionally possible to use the drive and dosing device a number of times, i.e., to exchange an empty product container for a full product container.

The housing is preferably intended to be held by the user of the device. In particular, the housing can have an essentially cylindrical shape. The housing can optionally have an indicator device, in particular a window, by means of which or through which a currently selected dose can be read, preferably from a dose scale of a dose selection element, which can be optionally present with the device.

The drive and dosing device comprises a dose selection member, which is made as a dosing button, for example. The dose selection member can preferably be held by the user (patient, physician, medical personnel) of the drive and dosing device and preferably forms an external, especially externally accessible, surface of the drive and dosing device. To select the dose to be discharged or administered, the dosing member is preferably held by the user and turned, relative to the housing and in particular the optionally present indicator device, about an axis of rotation that preferably corresponds to the lengthwise axis of the elongated, for example, drive and dosing device. The sleeve-shaped, for example, dose selection member can preferably be connected to the housing in an axially fixed way, so that advantageously intuitive handling of the device by the user is facilitated, since he merely needs to make a rotary movement of the dosing member to select a dose.

The drive and dosing device comprises a driven member, which is accommodated in the housing and can preferably be designed as a piston rod. The elongated driven member may extend along the lengthwise axis of the drive and dosing device. The distal end of the driven member can, for example, have a plate-shaped flange. The distal end of the driven member is disposed so that it can act on a piston of a product container, which can be affixed to the drive and dosing device, in particular by means of the product container holder. The driven member can move the piston of the product container to discharge the product in the product container when the driven member is moved in the distal direction relative to the housing.

The drive and dosing device comprises a driving member, which is rotatable relative to the housing and preferably about the lengthwise axis and is coupled to the driven member during the product discharge so that a rotation of the driven member causes the driven member to move in the distal direction relative to the housing.

The drive and dosing device according to the invention comprises a drive spring that is rotary or pretensioned with a torque, which is connected between the dose selection member and the driven member during the selection of the product dose, in particular when an actuation member is unactuated, and the dose selection member is non-rotatably coupled to the driven member during the selection of the product dose, in particular when the actuation member is unactuated. Advantageously, through this, a rotation of the driven member relative to the dose selection member, preferably in a first and second direction of rotation, is prevented during the selection of the product dose that is to be discharged. Through the positioning of the drive spring between the dose selection member and the driven member in accordance with the invention, the area around the driven member can be designed in a space-saving way or more space can be made available for possible additional components that, for example, give the drive and dosing device additional functions. Since the pretensioned drive spring is not further tensioned during dose selection, it becomes possible for the user to make a dose selection with less physical effort. A tensioning or slackening of the drive spring, which is connected between the dose selection member and the driven member during the selection of the product dose, is advantageously prevented by the fact that the dose selection member is coupled non-rotatably to the driven member during the selection of the product dose. A torque that attempts to rotate the driven member relative to the dose selection member and acts between the dose selection member and the driven member due to the rotationally tensioned drive spring, which can also be called a rotary or torsion spring, cannot rotate the driven member relative to the dose selection member, since the dose selection member is coupled non-rotatably to the driven member during the selection of the product dose. In particular, the drive spring is neither tensioned nor slackened during the selection of the dose during the rotation of the dose selection member in a first direction of rotation and/or in a second direction of rotation.

The at least one drive spring, which serves as the discharge spring, can be a helical or coil spring, which acts as a rotational or torsion spring. Especially preferably, the drive spring can be a spring wound in a spiral from a strip material, which can, for example, be called a spiral or clock spring. A rotationally pretensioned spring tries to rotate the parts on which it rests relative to each other.

In the as-delivered state of the drive and dosing device, the drive spring is pretensioned, in particular, with sufficient spring energy that it can discharge the maximum or total amount of product that can be discharged from the product container in a plurality of individual discharges, i.e., in particular in a plurality of discharges of single product doses, in particular completely. The drive and dosing device is designed so that after every individual discharge or discharge of the product dose the next dose to be discharged is selected anew. In contrast to embodiments in which the drive spring is tensioned anew with each dose selection, an easier dose selection can be achieved through the spring that is pretensioned with the energy needed for discharge of the maximum amount of product that can be discharged from the product container, since the dose selection member that is rotatable relative to the housing for dose selection is then easier to rotate, since the spring does not need to be tensioned during dose selection. This increases the ease of use for the user of the device.

Preferably, during the selection of the product dose, the dose selection member and the driving member can be rotated together, in particular relative to the driven member and/or relative to the housing. Preferably, a rotation of the dose selection member and preferably also the driving member during the selection of the product dose in a first direction of rotation brings about an increase of the dose to be discharged and said rotation in a second direction of rotation, which is opposite to the first direction of rotation, brings about a reduction of the product dose to be discharged. In embodiments in which a dose display is provided, a count-up of scale values in an indicator device would be seen during the rotation in the first direction of rotation, while during the rotation in the second direction of rotation, a count-down of the scale values would be seen in the indicator device.

Preferably, a rotation member can be disposed in a way that affects the movement, i.e., kinematically or operably connected, between the drive member and the driven member. The preferably sleeve-shaped rotation member can surround the driven member. The rotation member is preferably connected to the housing in an axially fixed and rotatable way. Preferably, the housing or the part affixed to the housing and the rotation member intermesh so that the rotation member is rotatable relative to the housing and is axially fixed.

In a first variation, the rotation member can be in a threaded engagement with a thread of the driven member. For example, the driven member can have an internal thread and the rotation member an external thread, which intermesh. Preferably, the rotation member can have an internal thread and the driven member an external thread, which intermesh.

The driven member can be engaged with a housing-affixed guide of the drive and dosing device. For example, the housing-affixed guide can be a lobe or a non-round cross section that fits into a groove or a non-round cross section of the driven member. For example, the groove or the non-round cross section can extend parallel to the lengthwise axis of the elongated driven member. The housing-affixed guide can be formed by the housing itself or by a part that is connected to the housing non-rotatably and axially fixed. The part can be connected to the housing permanently or can be non-rotatably and axially fixed at least during the product discharge. The groove or the non-round cross section of the driven member can, as an alternative to the design in which it runs parallel to the lengthwise axis, run helically or spirally about the lengthwise axis, but with a different pitch than the thread. These variations result in a rotation of the rotation member causing a movement of the driven member in the distal direction, in particular when the rotation member is rotated relative to the housing in the second direction of rotation. In this case, the driven member can screw either in the distal direction, in particular if the groove or the non-round cross section of the driven member is helical, or move linearly, in particular when the groove or the non-round cross section runs parallel to the lengthwise axis.

In a second variation, a housing-affixed internal thread can be in a threaded engagement with an external thread of the driven member. The driven member can move along the lengthwise axis and be non-rotatable relative to the rotation member. A rotation of the rotation member causes a screwing motion of the driven member in the distal direction. The driven member can have a non-round cross section or a groove, which engages with a non-round cross section or a projection of the rotation member.

Generally preferably, a rotation of the driving member relative to the housing and/or the dose selection member during product discharge or when the actuation member is actuated causes the driven member to be moved relative to the housing in the distal direction. In particular, a rotation of the driving member relative to the housing and/or the dose selection member causes the rotation member, which is operably connected between the driving member and the driven member, to rotate together with the driving member, i.e., to be moved relative to the housing and/or the dose selection member. The rotation of the rotation member causes a movement of the driven member in the distal direction. The driven member is moved in the distal direction relative to the housing in particular only during product discharge.

The drive and dosing device can have an actuation member, for example in the form of an actuation button. The actuation member can in particular be disposed at the proximal end of the drive and dosing device or can form the proximal end of the drive and dosing device. The actuation member can form an outer surface of the drive and dosing device and/or be externally accessible. The actuation member can advantageously be actuated, in particular pressed, with the thumb of the hand that holds the housing. The actuation can be stopped by releasing the actuation member. "Actuation" is understood to mean the movement of the actuation member in the drive and dosing device or the housing or dose selection member, in particular in the distal direction, so that a product discharge can be produced. The actuation member is advantageously movable along the lengthwise axis relative to the dose selection member and can in particular be accommodated in an axially movable way by the dose selection member.

The actuation member can be movable from an unactuated position, which it takes during the selection of the product dose to be discharged, to an actuated position, which it takes during the product discharge. In other words, the actuation member is in the actuated position during product discharge and the unactuated position during dose selection.

The actuation member can advantageously be movable, in particular actuatable, against the force of a spring, in particular a reset or coupling spring, where the said spring acts on the actuation member so that it becomes tensioned when the actuation member is moved from its unactuated position to its actuated position. By means of the reset spring, the actuation member is returned or moved from its actuated position to its unactuated position, in particular with a movement in the proximal direction relative to the dose selection member and/or the housing.

The drive and dosing device can preferably have a first coupling, which is disposed between, in particular operably connected between, the driving member and the driven member. In particular, the first coupling can be disposed between the driving member and the rotation member. The first coupling is uncoupled during the selection of the product dose or when the actuation member is unactuated, so that the driving member is able to be rotated relative to the driven member. During product discharge or with the actuation member actuated, the first coupling is coupled. This results in particular in the rotation member and the driving member being non-rotatably connected. The rotation member can thus rotate together with the driving member. The first coupling can comprise a first coupling structure, which is connected non-rotatably to the driving member, in particular is formed by the driving member, and a second coupling structure, which is connected non-rotatably to the rotation member, in particular is formed by the rotation member. The first coupling structure can be or can have a gear structure, and the second coupling structure can be or can have a gear structure. The gear structures of the first coupling structure and the second coupling structure can intermesh positively, and for instance form a clutch, when the first coupling is coupled. For example, the first coupling structure can be an internal gear structure, and the second coupling structure can be an external gear structure. Alternatively, the first coupling structure can be an external gear structure, and the second coupling structure can be an internal gear structure.

The drive and dosing device preferably has a second coupling, which is disposed between the dose selection member and the driving member. The second coupling is coupled during the selection of the product dose or when the actuation member is unactuated, so that the dose selection member and the driving member are non-rotatable with respect to each other. During product discharge or with the actuation member actuated, the second coupling is uncoupled, so that the driving member is rotatable relative to the dose selection member by means of the pretensioned drive spring.

The second coupling can have a third coupling structure, which is connected non-rotatably to the dose selection member, in particular is formed by the dose selection member, and a fourth coupling structure, which is connected non-rotatably to the driving member, in particular is formed by the driving member. The third coupling structure can be or can have a gear structure, and the fourth coupling structure can be or can have a gear structure. The gear structures of the third coupling structure and the fourth coupling structure can intermesh positively, and for instance form a clutch, when the second coupling is coupled. The third coupling structure can be an internal gear structure, and the fourth coupling structure can be an external gear structure. Alternatively, the third coupling structure can be an external gear structure, and the fourth coupling structure can be an internal gear structure.

In particular, the first and the second couplings can be matched to each other so that the actuation member can take an intermediate position between the unactuated position and the actuated position, for example a first intermediate position, in which the first coupling is coupled and the second couple is coupled. This advantageously results in the rotation of the driving member being released by the drive spring only when it has been ensured that the rotation member is non-rotatably coupled to the driving member. This advantageously avoids an erroneous operation of the device that could arise if the first coupling were not yet coupled and the second coupling were already uncoupled.

Preferably, the drive and dosing device can have a third coupling, which is disposed between, in particular operably connected between, the dose selection member and the housing. The third coupling is uncoupled during the selection of the product dose or with the actuation member unactuated, so that the dose election member is rotatable relative to the housing. The third coupling is coupled during product discharge or with the actuation member actuated, so that the dose selection member cannot rotate relative to the housing. It is generally preferred that the dose selection member cannot rotate relative to the housing during product discharge. This advantageously results in a dose selection not being possible during product discharge on the one hand and for the drive spring to rest indirectly against a segment on the housing.

The third coupling can be formed between the actuation member and the housing, where it is preferred that the actuation member and the dose selection member be connected non-rotatably, in particular permanently non-rotatably, or be connected non-rotatably at least during the selection of the product dose and during the product discharge.

The third coupling can have a fifth coupling, which is connected non-rotatably to the housing, in particular is formed by the housing, and a sixth coupling structure, which is connected non-rotatably to the dose selection member, in particular is formed by the dose selection member or the actuation member. The fifth coupling structure can have or be a gear structure, and the sixth coupling structure can have or be a gear structure. The gear structures of the fifth coupling structure and the sixth coupling structure can intermesh positively, and for instance form a clutch, when the third coupling is coupled. The fifth coupling structure can be an external gear structure, and the sixth coupling structure can be an internal gear structure. Alternatively, the fifth coupling structure can be an internal gear structure, and the sixth coupling structure can be an external gear structure.

The drive and dosing device can preferably have a rotation inhibiting device, which, during the selection of the product dose, especially when the actuation member is unactuated, keeps the rotation member from being rotatable relative to the housing, in particular relative to a shift member that is connected to the housing in a non-rotatable and axially movable way. The rotation inhibitor device can be operably connected between the housing, in particular the shift member, and the rotation member. The rotation inhibiting device can be a fourth coupling. The fourth coupling is coupled during the selection of the product dose or with the actuation member unactuated, so that the rotation member is non-rotatable relative to the housing. During the product discharge or with the actuation member actuated, the fourth coupling is uncoupled, so that the rotation member can rotate relative to the housing.

The fourth coupling can have a sixth coupling structure, which is connected non-rotatably to the housing, in particular is formed by the housing or the shift member, and an eighth coupling structure, which is connected non-rotatably to the rotation member, in particular is formed by the rotation member. The seventh coupling structure can be or can have a gear structure, and the eighth coupling structure can have or be a gear structure. In a preferred example, the gear structure of the second coupling structure can be the gear structure of the eighth coupling structure. In other words, this gear structure can form the second and the eighth coupling structures. For the sake of completeness it should be noted that the second and eighth coupling structures can, alternatively, be separate gear structures.

The gear structures of the seventh coupling structure and the eighth coupling structure can intermesh positively, and for instance form a clutch, when the fourth coupling is coupled. The seventh coupling structure can be an external gear structure, and the eighth coupling structure can be an internal gear structure. Alternatively, the seventh coupling structure can be an internal gear structure, and the eighth coupling structure can be an external gear structure.

Alternatively, the rotation inhibiting device can be a snap means formed by the rotation member, which is preferably formed in an elastically bendable way by the rotation member, and a gear structure, preferably an internal gear structure, which is non-rotatable with respect to the housing, in particular is formed by the housing or the shift member. The snap means can mesh into the gear structure, and the rotation member can be rotated relative to the housing or the shift member only after overcoming a certain limiting torque. The limiting torque can be designed so that it can easily be overcome by a torque that is provided through the rotationally pretensioned drive spring during the product discharge.

In a preferred embodiment, both the fourth coupling and the snap means meshing into the gear structure can be present, and the engagement of the snap means serves not as a rotation inhibiting device, but rather only to generate an acoustic and/or tactile signal during product discharge.

The couplings or coupling structures described herein can be moved or coupled to each other positively by movements along the lengthwise axis of the drive and dosing device. Preferably, the driving member can move back and forth along the lengthwise axis due to actuation and release of the actuation member, so that the first coupling structure and the fourth coupling structure and—if present—the seventh coupling structure are moved along the lengthwise axis. By actuation of the actuation member, the sixth coupling structure in particular is also moved in the distal direction along the lengthwise axis relative to the housing.

Preferably, the actuation member can take another intermediate position, in particular a second intermediate position, in which the third coupling and the second coupling are coupled. This advantageously ensures that the drive spring is operably linked between the housing and the driving member before the rotation of the driving member relative to the housing is released.

In particular, the optionally present fourth coupling can be the last of the couplings, which is coupled when the actuation member is moved from its unactuated position to its actuation position. Because of this, the uncoupling of the fourth coupling connects the torque of the drive spring to the rotation member, so that the rotation member is rotated.

In particular, it is generally preferred that the drive spring be connected between the dose selection member and the driving member during the dose selection and that it be connected between the housing and the driving member during the product discharge. In particular, the third coupling takes the function of the switch.

The drive spring can have a first segment, by which it is supported non-rotatably with respect to the dose selection member during the selection of the product dose to be discharged or with respect to the housing during the product discharge, a second segment by which it is supported non-rotatably with respect to the driving member, and a third segment, which is disposed between the first segment and the second segment and which becomes elastically deformed when there is a change of the spring tension of the drive spring. Preferably, the first segment and the second segment are rotated relative to the housing when the dose selection member is rotated relative to the housing. In particular, the first segment and the second segment can be fixed with respect to each other when the dose selection member is rotated for dose selection. Due to this, the spring tension does not change during the dose selection. The first segment can be affixed to the actuation member or can fit closely to it. The second segment can be affixed to the driving member or can fit closely to it.

Preferably, the actuation member surrounds the drive spring and/or a pin-shaped, for example, segment of the driving member. The drive spring can surround the segment of the driving member. Especially preferably, the drive spring can be accommodated in the actuation member and be affixed and/or fit closely to the driving member and in this way be braced indirectly at the dose selection member and/or the housing, in particular in each case according to the switching state of the third coupling.

A device that in particular reduces the friction between the actuation member and the driving member when the driving member rotates relative to the actuation member during the product discharge can be disposed between the driving member and the actuation member. The device can, for example, be such that the proximal end of the driving member, in particular the segment at which the discharge spring is affixed, tapers to a contact surface of the actuation member, and between the proximal end of the driving member and the contact surface there is a gap when the actuation member is in its unactuated position and the proximal end of the driving member fits closely to the contact surface when the actuation member is in its actuated position. On the one hand, this can result in the actuation member carrying the driving member during the shift of the actuation member into its actuated position, so that the first and the second couplings are coupled or uncoupled. Through the contact of the driving member with the actuation member, there arises friction between the driving member and the actuation member when the driving member rotates relative to the actuation member. This friction can be reduced through the said arrangement. The proximal end can, for example, be made in the form of a cone, a truncated cone, or a sphere. Alternatively, the contact surface can be made of a friction-reducing insert disposed between the driving member and the actuation member. The friction-reducing insert can, for example, be an insert of a friction-reducing plastic such as Teflon, POM, or the like. Alternatively, a roller bearing, in particular an axial roller bearing, or an axial ball bearing can be disposed between the driving member and the actuation member.

In preferred embodiments, the actuation member can have an engagement member, which keeps the driving member from being moved in the distal direction relative to the actuation member, for example by the reset spring, when the actuation member is unactuated. For example, the engagement member can engage in the driving member so that the said movement is prevented. The driving member can, for example, have an annular, circumferential collar that engages the actuation member, in particular the engagement member.

Generally preferably, the reset spring can be disposed between the dose selection member and the actuation member, in particular, can rest at one end, in particular its distal end, at the dose selection member, and at the other end, in particular the proximal end, at the actuation member. The reset spring can in particular be a helical spring that acts as a compression spring.

For example, the drive spring can be affixed in the, for example, pin-shaped segment of the driving member, which is disposed between the distal end of the driving member and the annular, circumferential collar.

The actuation member can, for example, be made in a plurality of parts, for example two parts, where it can have a connecting member, which is made, for example pot-shaped and in which the drive spring is inserted, where the connection member is closed at its distal end by means of a cap. The cap can form the contact surface, for example, for the thumb of the user of the drive and dosing device. The connecting member can, for example, have the sixth coupling structure and/or the engagement member, which encompasses the collar of the driving member.

Especially preferable embodiments of the drive and dosing device comprise a dose display element, which has a dose scale on its outer circumference and is connected to the driving member non-rotatably, in particular permanently, i.e., during the product discharge and dose selection. The dose display element thus participates in the rotary movements of the driving member. For example, the driving member and the dose display element can intermesh so that the driving member and the dose display member cannot rotate relative to each other and can be moved along the lengthwise axis. The housing has an indicator device, in particular a window. A scale value of the dose scale, which corresponds with the selected dose, can be read through the indicator device. The dose display element can, for example, be ring-shaped in cross section. The dose display element can, for example, be a dose display drum or dose display ring. The dose scale can extend over the circumference of the dose display element, preferably helically. The dose scale preferably comprises a plurality of dose values, which are arranged in succession and which give the dose scale. Preferably these are numerical values that indicate the desired product dose in international units (IU) or in milligrams.

Alternatively, the dose scale can be disposed without a pitch over the circumference of the dose display element, for example the dose display ring, where the scale values then repeat after one rotation of the dose display element. In the case of a dose scale with pitch, i.e., a helical dose scale, the dose display element, in particular the dose display drum, can be rotated more than one revolution without the scale values repeating, so that advantageously the scale values can represent larger or more scale values.

For selection of the dose to be administered, the dose display element can be rotated relative to the indicator device and in particular about an axis of rotation, which preferably corresponds to the lengthwise axis of the drive and dosing module and/or the dose display element. This can be a pure rotational movement, i.e., a rotational movement without superimposed axial movement. Preferably, the rotational movement is superimposed by an axial movement, so that the dose display element can be screwed relative to the indicator device to select the dose to be administered. A screwable dose display element can advantageously be combined with a helical dose scale, and the screwing movements and the dose scale advantageously have the same pitch. A dose display element that can be rotated without axial movement can advantageously be combined with a zero-pitch dose scale.

A value of the dose scale that corresponds to the selected dose can be read by means of the dose indicator, which preferably is formed on the housing. The indicator device can, for example, be a window, which can be formed by a penetration in the housing or by a transparent insert. Alternatively or optionally, the indicator device can be an arrow or have an arrow, which, for example, in addition to the window marks the value of the dose scale that corresponds to the selected dose. This is advantageous, for example, when another value still appears at least partly in the window, in order to guarantee an unambiguous dose selection. The indicator can, for example, be a projection, or a printed mark, or a notch, or the like.

In particular, the dose display element can be connected or coupled to the dose selection element in a non-rotatable, but, for example, axially movable way, during dose selection. For intuitive operation, it is advantageous if the dose display element, when the dosing member is rotated by an angle of rotation, is likewise rotated by the same angle of rotation.

The dose display element can have a thread, which engages with the housing or an element affixed to the housing or, alternatively, is in a threaded engagement with a shift member, which can also be called a bearing member, where the shift member is non-rotatable and movable along the lengthwise axis with respect to the housing. The threaded engagement advantageously produces the rotational or screwing movement of the dose display element relative to the indicator device. For example, the engagement between the dose display element and the shift member or housing can be a threaded engagement. In particular, the shift member can have an external thread and the dose display element an internal thread, where these threads intermesh and in this way cause the dose display element to be able to be screwed relative to the shift member.

In particular, the dose display element is rotatable or screwable back and forth between a maximum dose position and a zero dose position. In the zero dose position the dose or the number "zero" can advantageously be read in the display device. In the maximum dose position, the maximum product dose that can be discharged with the drive module can advantageously be read.

In the zero dose position, the dose display element can be blocked against turning in a direction of rotation, namely in the direction of rotation that would cause a dose less than zero to be selected. In the zero dose position, the dose display element can preferably be moved only in the direction of rotation, in particular in the first direction of rotation, that causes an increase of the dose. In the maximum dose position, the dose display element is preferably blocked against rotation in a direction of rotation, namely in the direction of rotation that would bring about the selection of a dose above the maximum selectable dose. In the maximum dose position, the dose display element can be rotated in particular only in the direction of rotation, in particular the second direction of rotation, that brings about a reduction of the product dose.

The dose display element can, for example, have a stop that in the zero dose position strikes a counterstop and thus prevents rotation in a direction of rotation. The same or an additional stop of the dose display element can prevent the rotation of the dose display element beyond the maximum dose. In particular, an additional counterstop, namely a maximum dose counterstop, can be provided for this. Accordingly, the other counterstop can be called the zero dose counterstop. The dose display element can thus have a zero dose stop for the zero dose counterstop and a maximum dose stop for the maximum dose counterstop. Preferably, the stop or stops act in the circumferential direction and/or in the axial direction.

The zero dose counterstop can be formed, for example, by the housing, in particular an element affixed to the housing, or the shift member. The maximum dose counterstop can be formed, for example, by the housing, in particular an element affixed to the housing, or the shift member.

The shift member can be movable together with the dose display element relative to the housing along the axis of rotation, in particular in the distal direction through actuation of the actuation member. Alternatively, the dose display element can have a thread, which engages with the housing or an element affixed to the housing. Through this, the dose display element can be screwed back and forth relative to the housing, but it cannot be moved independently from the screwing movement, in particular with a pure axial movement.

Preferably, the actuation member is coupled to the shift member so that a shift of the actuation member relative to the housing and/or the dosing member brings about a shift of the shift member relative to the housing and/or the dosing member, in particular along the lengthwise axis of the drive and dosing module. Generally preferably, the shift member and the driving member can be connected to each other, in particular intermeshed, so that the driving member is rotatable and axially fixed with respect to the shift member.

Because the dose display element is engaged with the shift member and the shift member can be moved relative to the housing and along the axis of rotation, the dose display element can also be moved relative to the housing and along the axis of rotation, independent of the rotary or screwing movement that the dose display element makes during dose selection. The drive and dosing device can however basically also advantageously be combined with the alternative dose display element that is in the threaded engagement with the housing or an element affixed to the housing. In this alternative, the shift element can preferably be non-rotatable and axially movable with respect to the housing.

Advantageously, one can read at the indicator device and/or the dose display element that the shift member was moved together with the dose display element. In this way, the user can monitor the operating state in which the drive and dosing device is, i.e., whether the drive and dosing device, in particular the actuation member, is actuated or unactuated for a discharge.

In a preferred variation, the actuation member and/or the shift member can be movable together with the dose display element relative to the indicator device, the housing, and along the axis of rotation. In the region of the indicator device, in particular in the window of the indicator device, a marking different from the dose scale can appear when the shift element has been moved. The marking is preferably disposed on the dose display element. If the shift element has not been moved, in particular the drive and dosing device is unactuated for the product discharge, the marking can be disposed outside of the indicator device, for example covered by a housing or another element. If the shift element is moved, in particular the drive and dosing device is actuated for product discharge, the marking can emerge from the covered region, so that it appears or is readable in particular at or in the indicator device. If the actuation of the drive and dosing device is interrupted or stopped, the shift member can be returned to the original position, so that the marking preferably becomes removed from the region of the indicator device and in particular becomes covered.

In an alternative variation, the actuation member and/or the shift member, together with the dose display element and the indicator device, can be movable relative to the housing and along the axis of rotation. The indicator device can, for example, be a lens or at least function as a lens. For example, the indicator device can be connected with the shift member at least axially fixed, preferably also non-rotatably. Basically, the shift member can form the indicator device. Of course, it is also possible for the indicator device to be a part that is separate from the shift member. The indicator device can, for example, be sleeve-shaped.

In this variation the movement of the shift member causes a marking that is different from the dose scale to appear in the region of the indicator device, the marking being disposed or formed at or on the indicator device. For example, the indicator device can be disposed within the housing. In the unactuated state of the drive and dosing device, the marking of the indicator device can be covered by the housing or another element. If the drive and dosing device, in particular the actuation member, becomes actuated, so that the dose and display element is moved together with the indicator device, the marking can emerge from its covering, so that the marking becomes visible or readable. If the actuation is interrupted or stopped, the dose display element together with the indicator device and the shift member can be moved back to their starting position, so that the marking again is disposed under the covering.

Generally preferably, a spring, in particular a coupling or reset spring, becomes tensioned during the actuation of the drive and dosing device for a product discharge. In other words, the shift member can be moved against the force of such a spring in particular during the actuation, in particular from an unactuated position to an actuated position. The spring can, for example, be a coil or helical spring that acts as a compression spring. The said spring further causes the shift member to be returned to its starting position or unactuated position if the actuation is interrupted or stopped. In particular, the shift member is moved in the distal direction during actuation. The shift member is moved back to the proximal direction by means of the spring if the actuation is interrupted or stopped.

BRIEF DESCRIPTION OF THE DRAWINGS

FIGS. 4A-4D show the drive and dosing device from FIGS. 3A-3D in a state in which the maximum dischargeable dose is selected, FIGS. 5A-5D show the drive and dosing device from FIGS. 3A-3D in an actuated state after the product discharge, FIGS. 9A-9D show various views of the drive and dosing device composed of the individual parts from FIG. 7 in an initial, as-delivered state.

DETAILED DESCRIPTION

Figure 1:
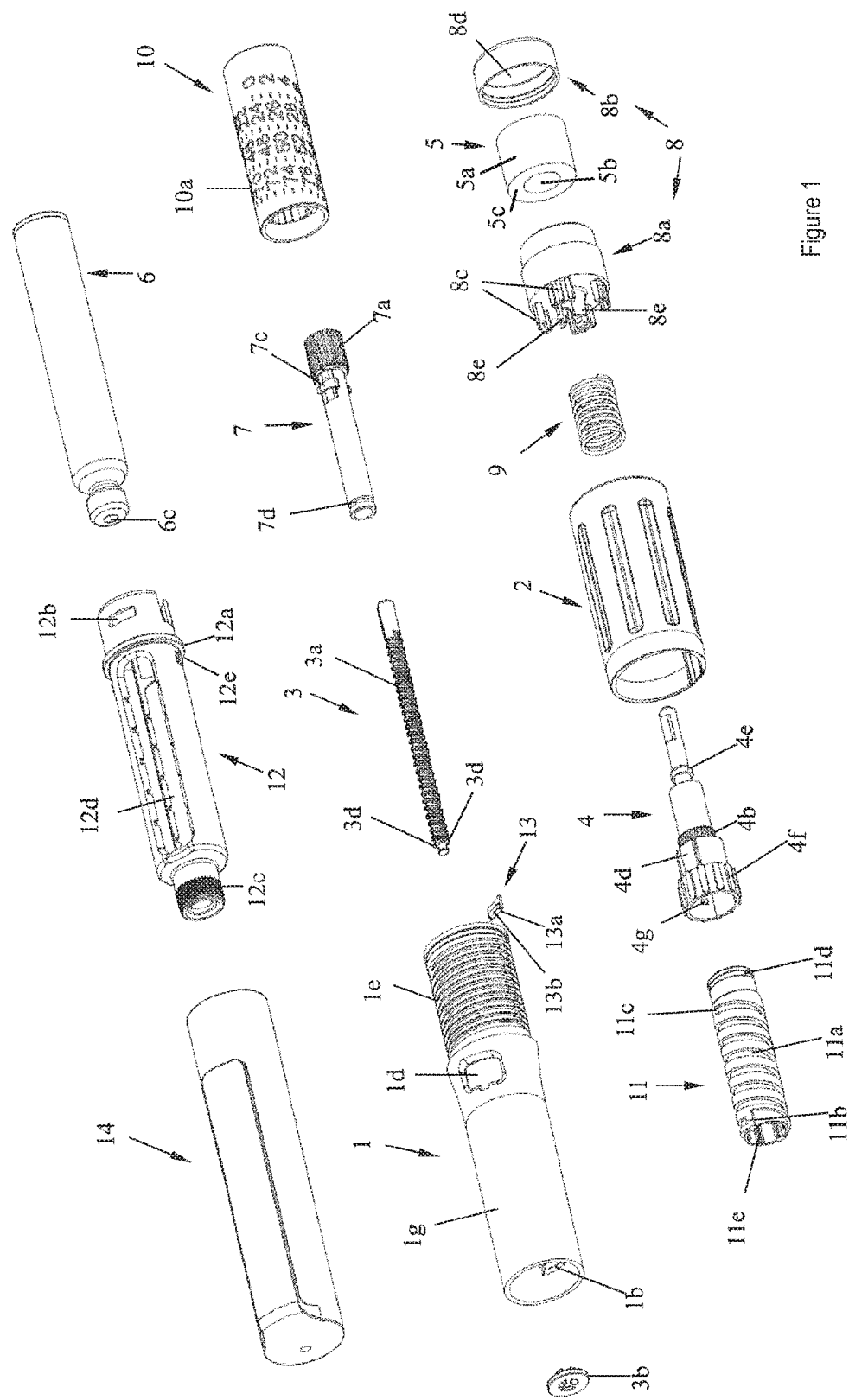
FIG. 1 shows an exploded drawing of the individual parts of the drive and dosing device according to the invention in a first embodiment.
Figure 2:
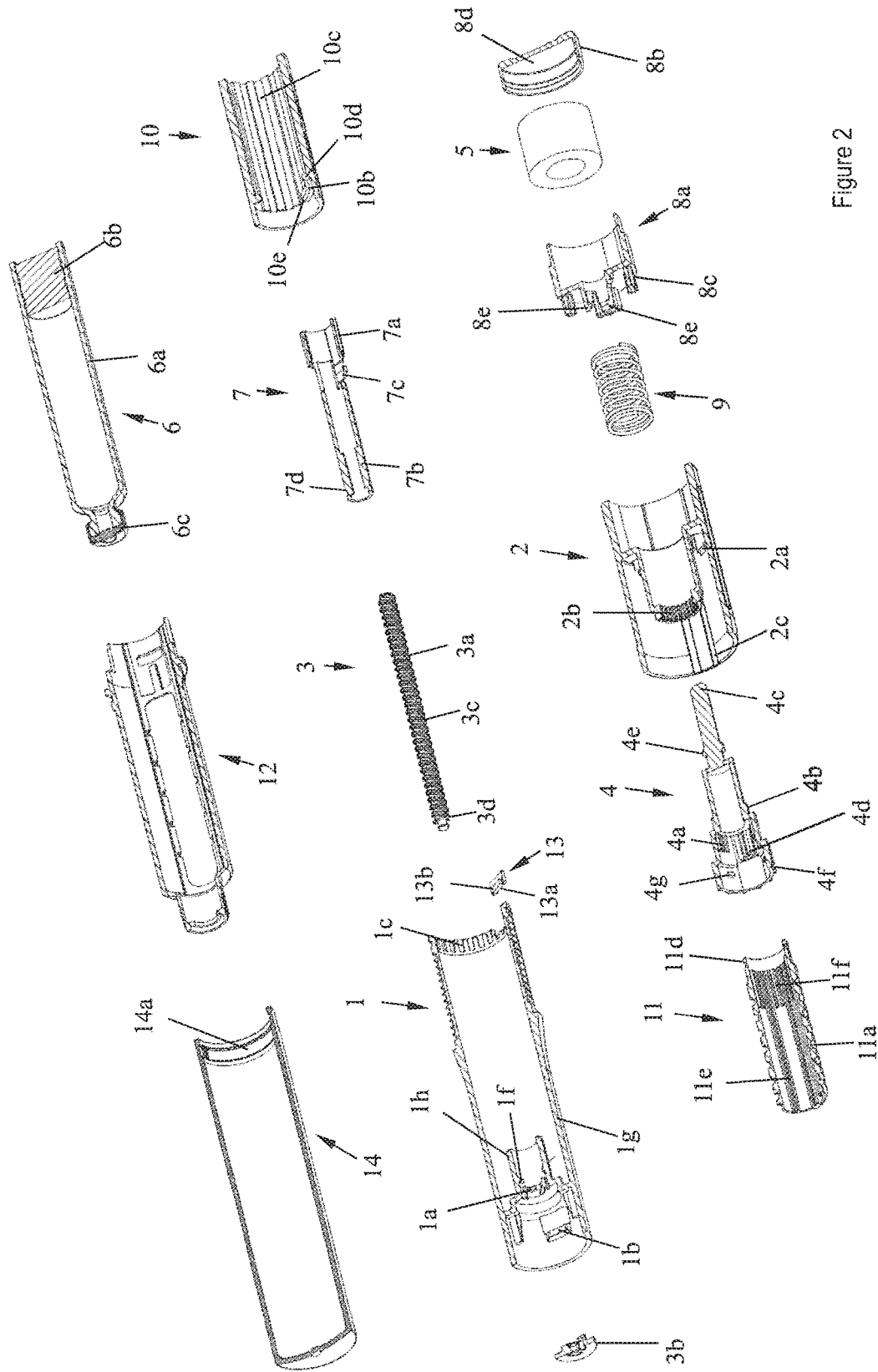
FIG. 2 shows the exploded drawing from FIG. 1, where the individual parts are shown in a sectional view.
Figure 8:
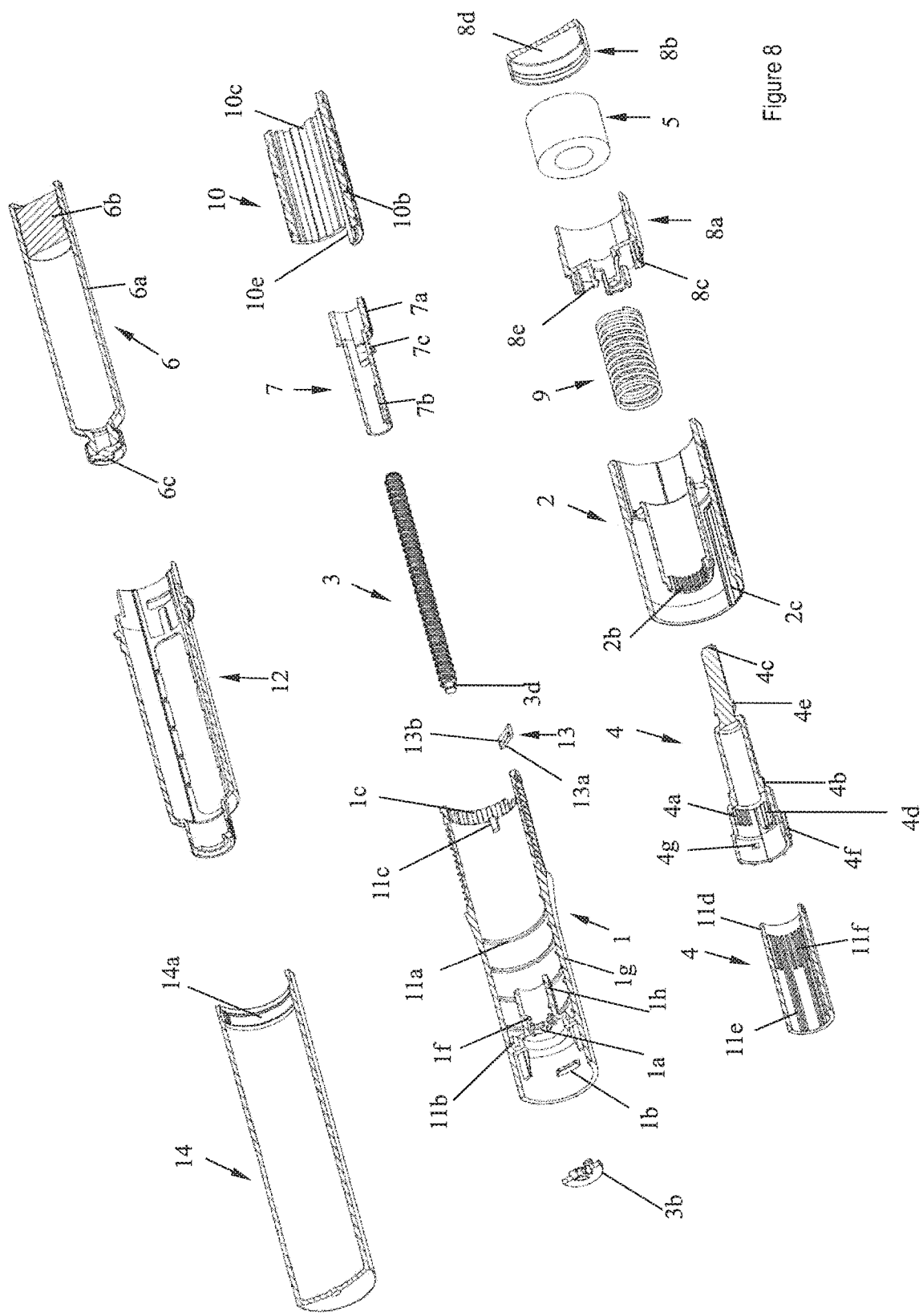
FIG. 8 shows the exploded drawing from FIG. 7, where the individual parts are shown in a sectional view.
Figure 10A:
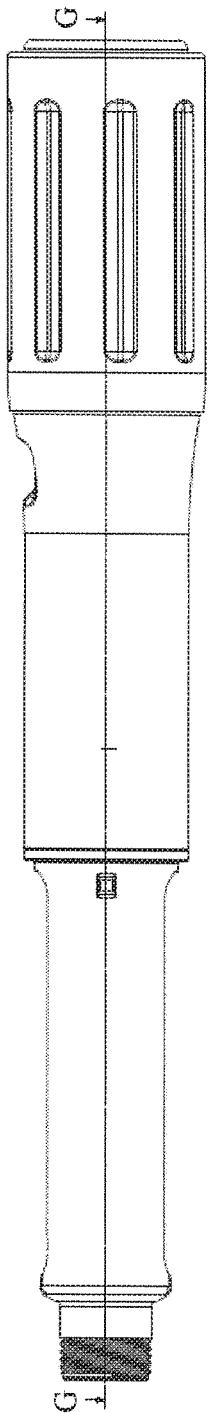
FIGS. 10A-10D show the drive and dosing device from FIGS. 9A-9D in an actuated state at the maximum selected dose.
Figure 10B:
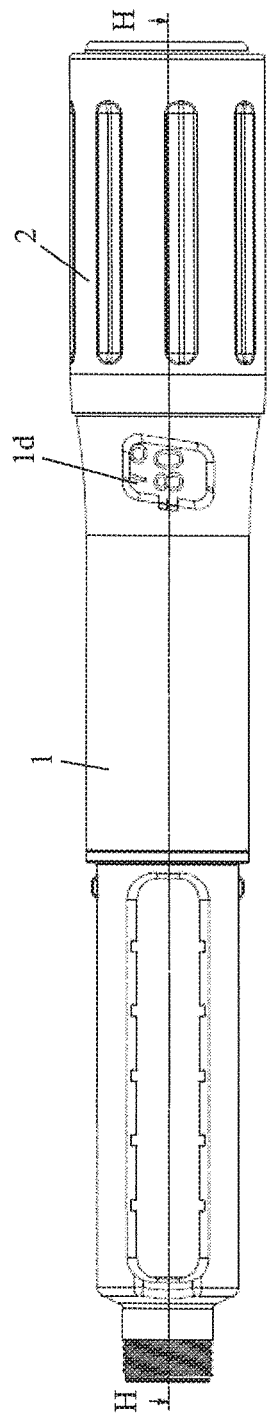
Figure 10C:
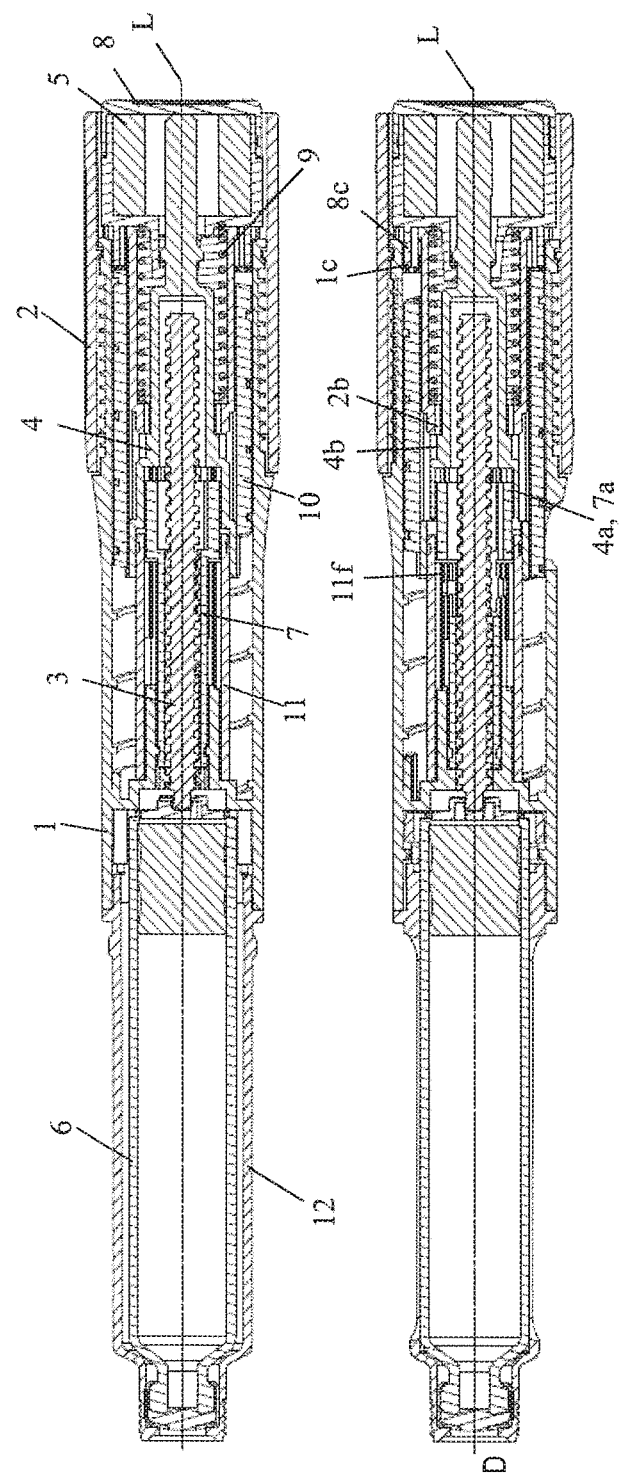
Figure 10D:
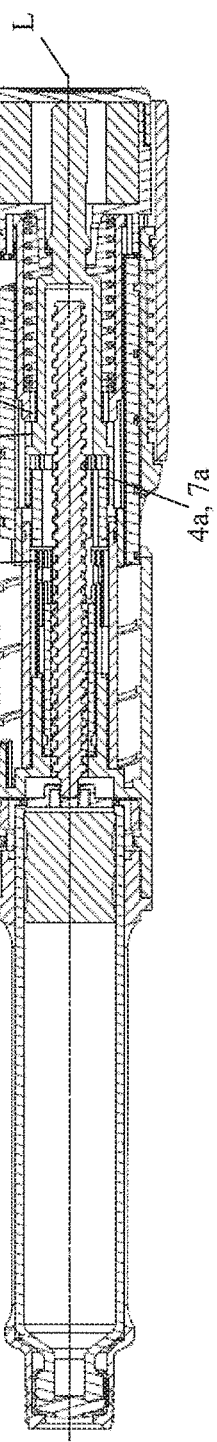

The first embodiment, shown in FIGS. 1 to 6D, and the second embodiment, shown in FIGS. 7 to 10D, differ essentially in the design of a dose display element 10 and a shift member 11. In the first embodiment, the dose display element 10 has an internal thread 10b, which meshes into an external thread 11a of the shift member 11 (FIG. 1). The second embodiment has a dose display element 10 that has an external thread 10b, which meshes in an internal thread 11a of the housing 1 (FIG. 8).

Unless otherwise indicated, the following description refers to the first embodiment and the second embodiment.

The drive and dosing device forms an injection device, or is at least part of such an injection device. The drive and dosing device has a sleeve-shaped housing 1, which has an outer sleeve 1g and an inner sleeve 1h that is connected to the outer sleeve and disposed concentrically to it. The inner sleeve 1h and the outer sleeve 1g are solidly connected via an annular web. The housing 1, in particular the inner housing 1h, has an internal thread 1a, which meshes into an external thread 3c of the threaded rod 3a, so that the threaded rod 3a and thus the driven member 3 can be screwed in the distal direction relative to the housing 1 and along the lengthwise axis L. The driven member 3 has the threaded rod 3a and a plate-shaped flange 3b, which is affixed in a freely rotatable way at the distal end of the threaded rod 3a, in particular is snapped onto it. The threaded rod 3a has at least one guide slot 3d, which overlays the external thread 3c and runs parallel to the lengthwise axis L. A sleeve-shaped rotation member 7 has, on its inner circumference, at least one web-shaped engagement member 7b, which meshes into the guide slot 3d, so that the rotation member 7 and the driven member 3 are non-rotatable and axially movable relative to each other. The rotation member 7 has, on its outer circumference, an annular slot 7d, in which a projection if formed on the inner circumference of the housing 1, in particular the inner sleeve 1h, meshes, so that the rotation member 7 is rotatable and axially fixed relative to the housing 1. A rotation of the rotation member 7 brings about a rotation of the driven member 3, so that the driven member 3 is movable along the lengthwise axis L because of the threaded engagement with the housing 1. For example, the driven member 3 is moved in the distal direction if the rotation member 7 is rotated in a second direction of rotation about the lengthwise axis L relative to the housing 1.

The rotation member 7 has a second coupling structure 7a in the form of an external gear structure.

The housing 1, in particular the inner housing 1h, has on its outer circumference an engagement structure, where the said engagement structure and a slot formed on the inner circumference of the shift member 11 or a fin-shaped lengthwise guide 11e intermesh so that the shift element 11 is non-rotatable about the lengthwise axis L and can be moved along the lengthwise axis L relative to the housing 1. The shift member 11 has, on its inner circumference, an internal gear structure 11f, in which a snap means 7c, which is made springy on the rotation member 7, engages. The snap means 7c has a snap arm, on the outer side of which an engagement lobe is disposed, which meshes into the internal gear structure 11f. Upon rotation of the rotation member 7 relative to the shift member 11, the snap means 7c moves over the internal gear structure 11f, so that the product discharge can be signaled, for example, by means of an acoustic and/or tactile signal.

The engagement of the snap means 7c in the internal gear structure 11f can in one variation be such that the rotation member 7 can be rotated only after overcoming a certain limit torque relative to the housing 1 or the shift member 11. Through this, the engagement of the snap means 7c in the internal gear structure 11f prevents the driven member 3 from unintended rotation relative to the housing 1, for example due to vibrations in the transport of the drive and dosing device. Through the matching of the snap means 7c and the internal gear structure 11f, the limit torque is set so that it can easily be overcome by a torque that is made available by a rotationally pretensioned drive spring 5 during the product discharge.

However, in the figures another preferred variation is shown, in which the snap means 7c and the internal gear structure 11f merely serve to generate an acoustic and/or tactile signal during product discharge. The internal gear structure 11f forms a seventh coupling structure, which meshes in the outer gear structure of the second coupling structure 7a. The second coupling structure 7a and the seventh coupling structure 11f form a fourth coupling 7a, 11f. Alternatively, the rotation member 7 can have an eighth coupling structure in the form of a gear structure, in particular an external gear structure, which, for example, is separate from the second coupling structure 7a. In this case, the seventh coupling structure 11f and the eighth coupling structure form the fourth coupling.

The fourth coupling 7a, 11f is coupled when the actuation member 8 is unactuated, and uncoupled when the actuation member 8 is actuated. If the fourth coupling 7a, 11f is coupled, the seventh coupling structure 11f and the second coupling structure 7a or the eighth coupling structure intermesh non-rotatably.

The shift member 11 has, at its proximal end, an annular groove 11d, in which a projection 4g on the inner circumference of a driving member 4 meshes, so that the driving member 4 is rotatable and axially fixed relative to the shift member 11. A movement of the driving member 4 along the lengthwise axis L thus also causes a movement of the shift member 11 along the lengthwise axis L. The driving member 4 has a first coupling structure 4a in the form of an internal gear structure, which forms a first coupling 4a, 7a with the second coupling structure 7a. From an uncoupled position, in which the first coupling structure 4a and the second coupling structure 7a do not intermesh, the driving member 4 can be moved into a coupled position along the lengthwise axis L, in which the first coupling structure 4a and the second coupling structure 7a intermesh positively. The driving member 4 can be rotated about the lengthwise axis L relative to the rotation member 7 when the first coupling 4a, 7a is uncoupled, and cannot be rotated about the lengthwise axis L relative to the rotation member 7 when the first coupling 4a, 7a is coupled.

The driving member 4 has a snap structure 4d, which is made springy on the drive member 4. The snap structure 4d has at least one tooth, which engages with a gear structure, in particular the second coupling structure 7a of the rotation member 7, when the first coupling 4a, 7a is uncoupled. The snap structure 4d snaps over the gear structure, in particular the second coupling structure 7a of the rotation member 7, when the driving member 4 is rotated in a first direction of rotation and/or a second direction of rotation relative to the rotation member 7 during the selection of a product dose to be discharged. This generates clicking sounds, which on the one hand signal the selection of the dose to the user in a tactile and/or acoustic way and on the other hand specify discrete angular positions for the driving member 4 with respect to the rotation member 7.

In the variation without the fourth coupling 7a, 11f, the engagement of the snap structure 4d in the rotation member 7 with respect to the engagement of the snap means 7c in the internal gear structure 11f is designed so that when the driving member 4 is rotated relative to the rotation member 7, the torque exerted due to this on the rotation member 7 is less than the limit torque that is necessary for a rotation of the rotation member 7 with respect to the shift member 11.

The driving member 4 has a fourth coupling structure 4b, which is designed as an external gear structure. The fourth coupling structure 4b, with a third coupling structure 2b that is designed as an internal gear structure, forms a second coupling 2b, 4b. A sleeve-shaped dose selection member 2 is affixed to the housing 1, and the dose selection member 2 is axially fixed and can be rotated relative to the housing 1. The dose selection member 2 has an outer sleeve and an inner sleeve, which are firmly connected to each other via a web. The dose selection member 2, in particular the outer sleeve, has on its inner circumference a projection 2a, which meshes into an annular groove of housing 1, in particular the outer sleeve 1g, so that the dose selection member 2 is axially fixed and can be rotated relative to the housing 1.

The dose selection member 2, in particular its inner sleeve, forms the third coupling structure 2b. The third coupling structure 2b meshes positively into the fourth coupling structure 4b when the second coupling 2b, 4b is coupled, so that the dose selection member 2 is connected to the driving member 4 non-rotatably about the lengthwise axis L. The driving member 4 thus participates in the rotary motions of the dose selection member 2. When the second coupling 2b, 4b is uncoupled, the third coupling structure 2b and the fourth coupling structure 4b do not intermesh, so that the dose selection member 2 and the driving member 4 can be rotated relative to each other.

To select a product dose that is to be discharged, the dose selection member 2 is rotated relative to the housing 1 in a first direction of rotation to increase the dose and in a second direction of rotation to reduce or correct the dose. During dose selection, the second coupling 2b, 4b is coupled, so that the driving member 4 follows the rotary motions of the dose selection member 2.

The dose selection member 2 is disposed at the proximal end of the housing 1 and can be held by the user of the device and can rotate relative to the housing 1.

The proximal end of the drive and dosing device is formed by an actuation member 8, which is designed as an actuation button. The actuation member 8 can be moved against the reset spring 9 from an unactuated position (for example, see FIGS. 3A-D and 9A-D) to an actuated position (for example, see FIGS. 5A-D and 10A-D), where the reset spring 9 is tensioned by this. The reset spring 9 is a helical or coil spring, which acts as a compression spring and rests at its distal end at the dose selection member 2 and at its proximal end at the actuation member 8. During actuation, the actuation member 8 is, for example, pressed with the thumb of the hand that holds housing 1, so that the spring 9 becomes tensioned. By releasing the actuation member 8, the pretensioned spring 9 can move the actuation member 8 from the actuated position to the unactuated position.

The actuation member 8 can move back and forth along the lengthwise axis L relative to the dose selection member 2, namely between the actuated position and the unactuated position. The actuation member 8 is made of a number of pieces and has a connecting member 8a, which has a sleeve-shaped segment, which is made narrower or is closed by an inwardly projecting collar at the distal end. The proximal end of the connecting member 8a is closed by means of a cap 8b, which also belongs to the actuation member 8 and forms a contact surface for the thumb in order to actuate the actuation member 8.

The actuation member 8, in particular the sleeve-shaped segment of the connecting member 8a, surrounds the drive spring 5 circumferentially. The drive spring 5 is a spring that is spiral-wound from a strip material, which can also be called a clock spring. A first segment 5a, in particular a first end of the drive spring 5, is affixed to the actuation member 8, in particular to its cylindrical segment. A second segment 5*b*, in particular a second end of the drive spring 5, is affixed to the driving member 4, in particular between its proximal end 4*c* and a collar 4*e*. Between the first segment and the second segment, the drive spring 5 has a third segment 5*c*, which becomes elastically deformed when there is a change of the spring tension. A rotation of the driving member 4 relative to the actuation member 8 causes a change of the spring tension, in particular a decrease of the spring tension while releasing the potential energy stored by the spring to the driving member 4 in the form of kinetic, i.e., rotational, energy. The driving member 4 has, in particular, a rod- or pin-shaped segment, which extends through the collar 8*e* at the distal end of the actuation member 8 into the inner part of the actuation member 8 and through the drive spring 5. The proximal end 4*c* tapers toward the proximal end of the drive and dosing device, for example in the shape of a sphere, cone, or truncated cone. The actuation member 8, in particular the cap 8*b*, forms a contact surface 8*d* for the proximal end 4*c* of the driving member 4.

The actuation member 8, in particular the connecting member 8*a*, has a sixth coupling structure 8*c* in the form of an external gear structure, which is formed, for example, at a projection projecting in the distal direction. The projection extends through the collar, which connects the inner sleeve to the outer sleeve of the dose selection member 2. The housing 1, in particular the outer sleeve 1*g*, has a fifth coupling structure 1*c*, which is made as an internal gear structure and, with the sixth coupling structure 8*c*, forms a third coupling 1*c*, 8*c*. The third coupling 1*c*, 8*c* can be coupled by actuation of the actuation member 8 and uncoupled by release of the actuation member 8. When the third coupling 1*c*, 8*c* is coupled, the sixth coupling structure 8*c* extends positively into the fifth coupling structure 1*c*, so that the actuation member 8 and in particular also the dose selection member 2, which is non-rotatably connected to the actuation member 8, cannot be rotated with respect to the housing 1. The actuation member 8 and the dose selection member 2 can be rotated relative to the housing 1 when the third coupling 1*c*, 8*c* is uncoupled, and the sixth coupling structure 8*c* and the fifth coupling structure 1*c* do not then intermesh.

A sleeve-shaped product container holder, in which a product container 6 is accommodated, is affixed, in particular inseparably, at the distal end of the housing 1. The product container 6 is a cartridge in the example shown. The product container 6 has a container body 6*a*, which surrounds a liquid product that is to be administered, and a movable piston 6*b* is disposed in the container body 6*a* proximal to the product, the piston fitting tightly against the inner wall of the container body 6. At the distal end of the container body 6*a*, there is a septum 6*c*, which can be punctured by a needle, which can be fitted to a thread 12*c* of the product container holder 12. With movement of the piston 6*b* in the direction of septum 6*c*, the product contained in the product container 6 is discharged via the needle.

The product container holder 12 has a window 12*d*, through which the amount of product contained in the product container 6 can be visually monitored. The product container holder 12 has a recess 12*b*, into which a first engagement structure 1*b* on the inner circumference of the housing 1, in particular the outer sleeve 1, is snapped when the product container holder 12 is affixed to the housing 1. The product container holder 12 has an annular collar 12*a* on its outer circumference that fits closely to the distal end of the housing 1, in particular the outer sleeve 1*g*, when the product container holder 12 is affixed to the housing 1. The product container holder 12 has a lobe 12*e* on its outer circumference, onto which a sleeve-shaped cap, which can slide over the product container holder 12, can be separably snapped. The cap 14 can thus be removed and serves only to protect an optionally fitted needle and/or the medication against the effect of light. In order to be snapped with the lobe 12*e*, the cap 14 has an annular recess 14*a* made on the inner circumference, in particular a groove.

The drive and dosing device has a dose limiter 13 in the form of a ring segment, alternatively a ring or a nut, which has on its inner circumference a threaded segment 13*b*, which meshes into a thread 1*e* disposed on the outer circumference of the housing 1 so that the dose limiter 13 can be screwed relative to the housing 4. The dose limiter 13 is held in a groove 2*c* that extends along the lengthwise axis L and is disposed on the inner circumference of the dose selection member 2, where the sides of the groove laterally hold in the ring segment-shaped dose limiter 13. On the outer circumference, the dose limiter 13 has a groove-shaped engagement member 13*a*, into which a lengthwise guide, which projects from the base of the groove 2*c* of the dose selection member 2 and extends along the lengthwise axis L, meshes. The dose limiter 13 cannot rotate relative to the dose selection member 2 both because of the groove 2*c* and the lengthwise guide, but it is axially movable. A limit stop is made on the dose selection member 2 or the housing 1, from which the dose limiter 13 is spaced in proportion to the maximum amount of product that can be discharged from the product container 6. Since during dose selection the dose selection member 2 is rotated relative to the housing 4 and is not rotated during dose discharge, a numerical value can be formed by the dose limiter 13 that adds up the already discharged single doses and the currently selected dose and correspondingly continuously approaches the limit stop of the dose selection member 2 or the housing 1. An increase of dose causes the dose limiter 13 to move toward the limit stop. A dose reduction causes the dose limiter 13 to move away from the limit stop. If the remaining dose indicated in the product container 6 is less than the maximum dose that can be selected with the drive and dosing device, the dose limiter 13 comes into contact with the limit stop, so that rotation of the dose selection member 2 relative to the housing 1 in a direction of rotation that would result in an increase of the dose, i.e., in a first direction of rotation, is blocked.

The dose display element 10, which is sleeve-shaped and thus can be called the dose display drum, has a helical dose scale 10*a* extending over its outer circumference in correspondence with the pitch of thread 10*b*, the dose scale comprising a plurality of successive scale values. In the two embodiments that are shown, a maximum dose of 80 IU can be selected with the drive and dosing device, and the scale runs from 0 to 80 and the dose values are given in steps of two.

The dose display element 10 has a stop surface pointing and acting in the circumferential direction, which is called the zero dose stop 10*e*. The dose display element has a stop surface that points and acts in the circumferential direction, which is called the maximum dose stop 10*d*.

In the embodiments in FIGS. 1 to 6D, the sleeve-shaped shift member 11 has an external thread 11*a*, in which the internal thread 10*b* meshes. The shift member 11 further has a zero dose counterstop 11*b* and a maximum dose counterstop 11*c*.

In the embodiment in FIGS. 7 to 10D, the thread 10*b* is an external thread, which engages an internal thread 11*a* of the outer sleeve 1g of the housing 1, or generally speaking the housing 1. The housing 1, in particular the outer sleeve 1g, has a zero dose counterstop 11b and a maximum dose counterstop 11c.

For both embodiments, the dose display element 10 can be screwed back and forth between a zero dose position and a maximum dose position. In the zero dose position, the zero dose stop 10e in combination with the zero dose counterstop 11b prevents the rotation of the dose display element 10 in a second direction of rotation, namely in a direction of rotation that would cause a smaller dose than zero to be selected. In the said zero dose position, the dose display element 10 can be rotated in the opposite, i.e., the first, direction of rotation.

In the maximum dose position, the maximum dose stop 10d in combination with the maximum dose counterstop 11c prevents the rotation of the dose display element 10 in a first direction of rotation, which would cause an increase of the dose beyond the maximally selectable value. Rotation in the second direction of rotation is possible in the maximum dose position.

The housing 1, in particular the outer sleeve 1g, has an indicator device 1d in the form of a window, which opens the view to the dose scale 10a of the dose display element 10. The dose display element 10 is connected to the driving member 4 non-rotatably and axially movable. For this, the dose display element 10 has at least one, in this example several, guide slots 10c, which run parallel to the lengthwise axis L. Projections 4f on the outer circumference of the driving member 4 mesh into the said guide slots 10c.

Figure 3A:
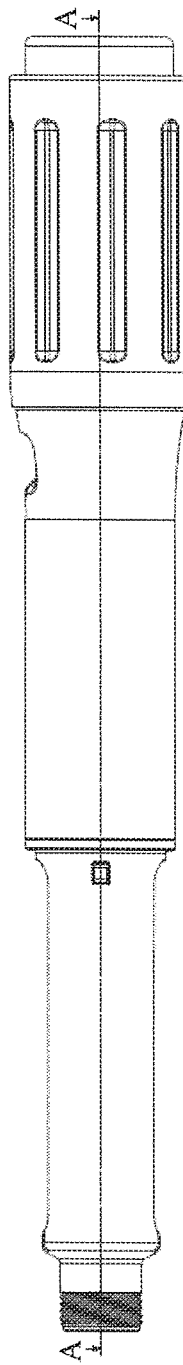
FIGS. 3A-3D show various views of the drive and dosing device composed of the individual parts from FIG. 1 in an initial, as-delivered state.
Figure 3B:
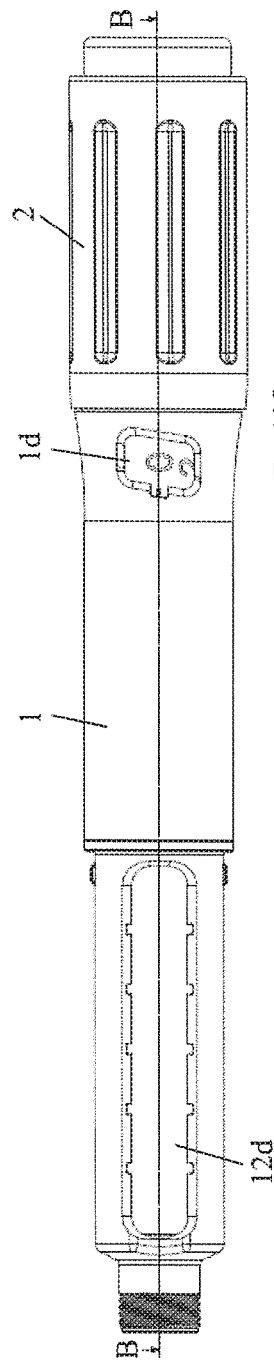
Figure 3C:
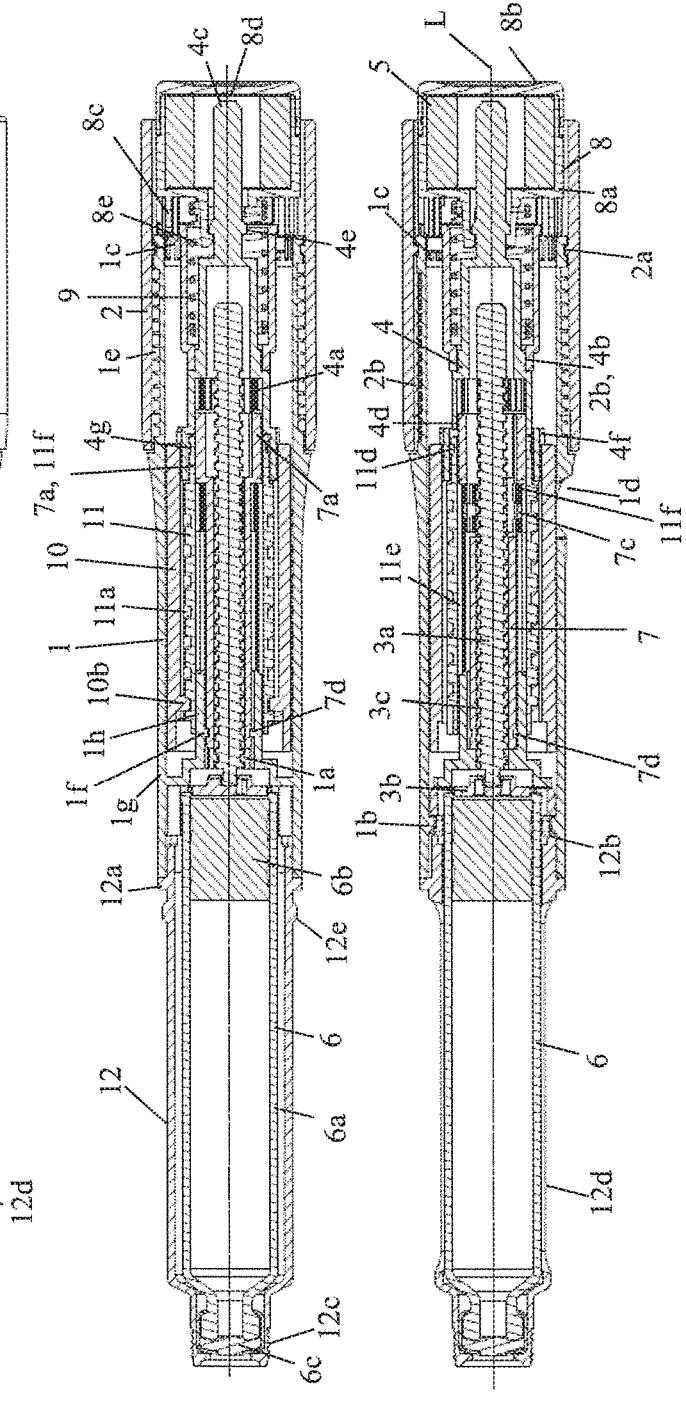
Figure 3D:
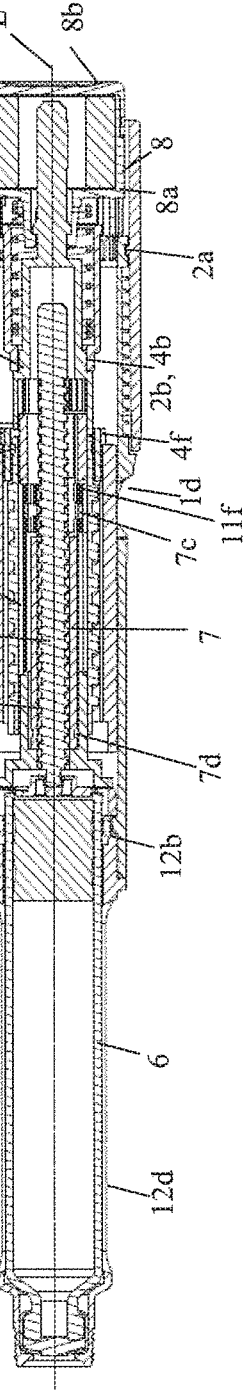
Figure 6A:
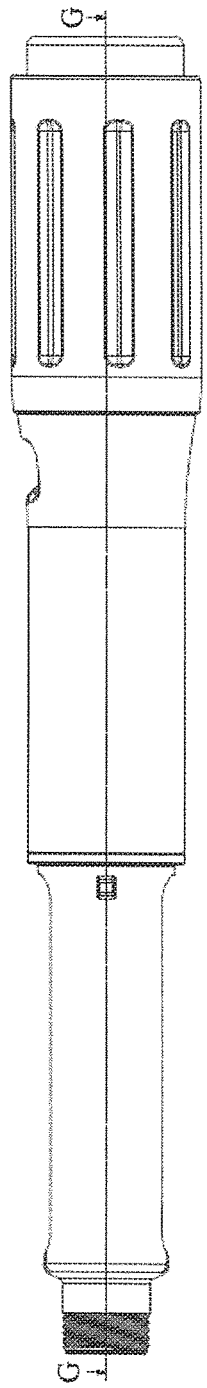
FIGS. 6A-6D show the drive and dosing device from FIGS. 3A-3D, in which the product contained in the product container has been completely discharged.
Figure 6B:
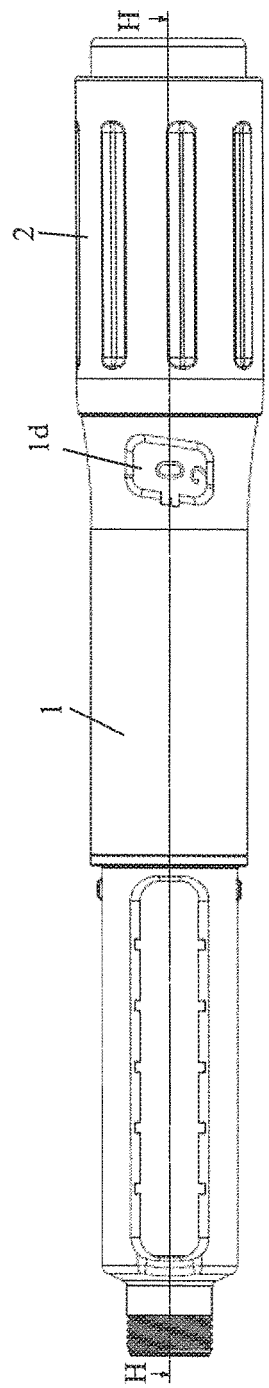
Figure 6C:
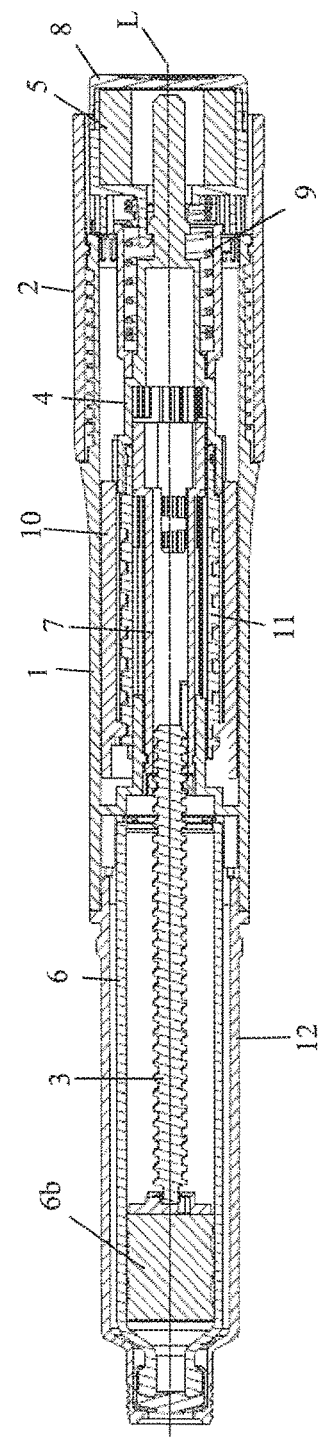
Figure 6D:
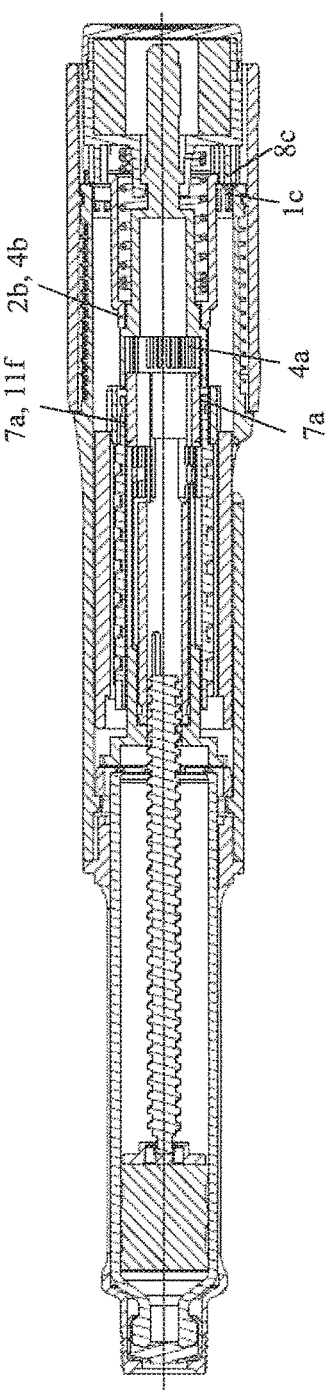
Figure 7:
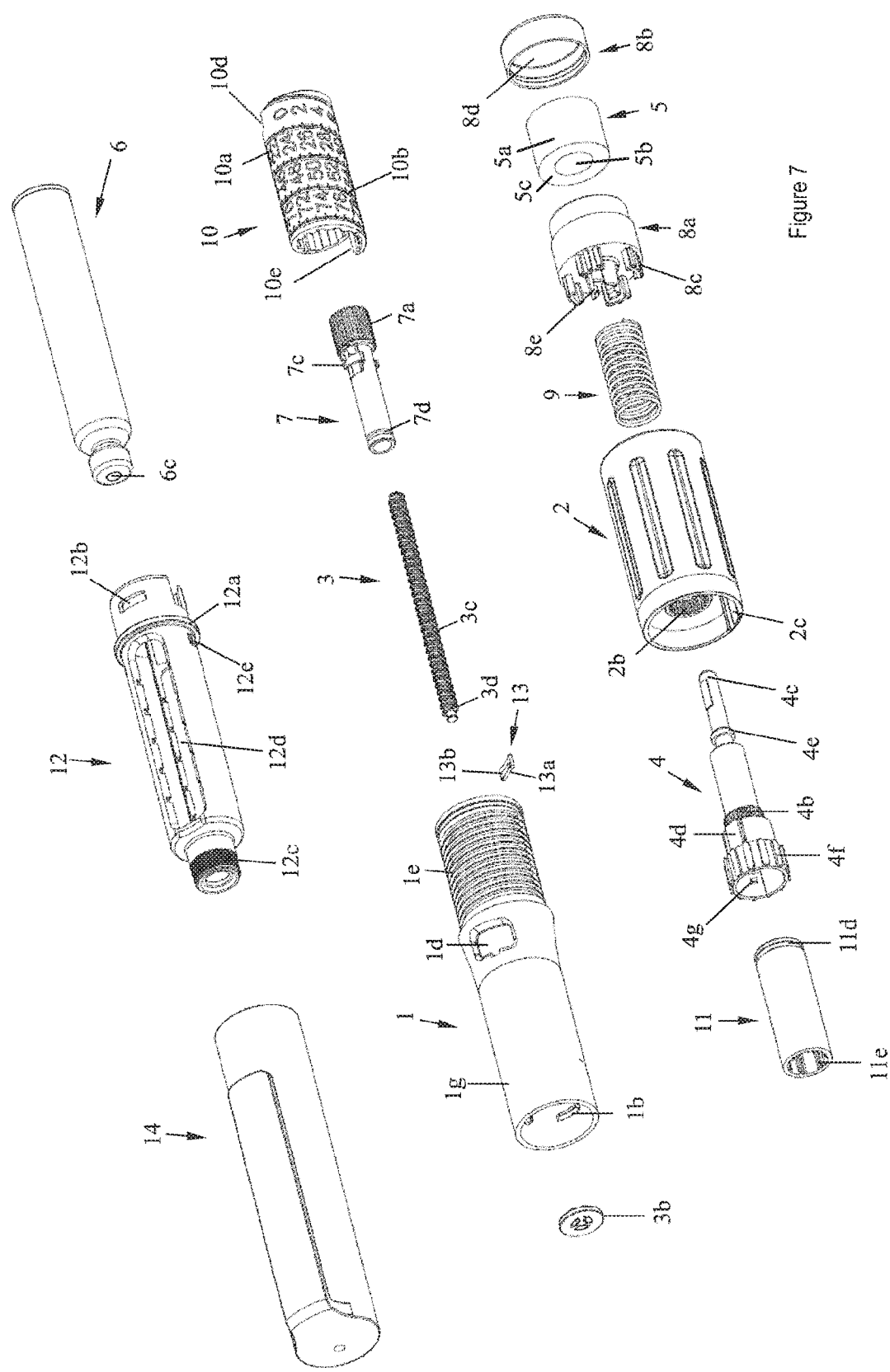
FIG. 7 shows an exploded drawing of the individual parts of a drive and dosing device according to the invention in a second embodiment.

In FIGS. 3A-D and 9A-D, the first and second embodiments are shown in their as-delivered or initial state, with cap 14 having been removed. The actuation member 8 is unactuated. In FIG. 3B, the dose appearing in the indicator device 1d is zero, i.e., the dose display element 10 is in its zero dose position.

The drive spring 5 is pretensioned with sufficient energy that the amount of product contained in the product container 6 can be completely discharged by moving the piston 6b with the energy stored in the spring 5, in particular in one or several individual discharges, between which a new dose selection takes place each time, without tensioning spring 5. In the initial, as-delivered state, the first coupling 4a, 7a is uncoupled, the second coupling 2b, 4b is coupled, and the third coupling 1c, 8c is uncoupled. The drive spring 5 is operably connected between the driving member 4 and the dose selection member 2. The coupling 2b, 4b keeps the driving member 4 from rotating relative to the dose selection member 2.

To select the product dose to be discharged, the dose selection member 2 is rotated relative to the housing 1 in a first direction of rotation, so that the driving member 4, spring 5, and dose display element 10 likewise are rotated together. Through the rotation, the dose display element 10 is screwed away from the zero dose counterstop 11b, and the distance measure between the zero dose stop 10e and the zero dose counterstop 11b along the curve of the screw is proportional to the product dose to be discharged. The currently selected dose can be read in IU through the indicator device 1d. If the dose is unintentionally set too high, the dose selection member 2 can be rotated in the opposite direction of rotation, i.e., in the second direction of rotation relative to the housing 1, so that the distance between the zero dose stop and the maximum dose stop decreases and the dose that is read is reduced.

For product discharge, the actuation member 8 is pressed from an unactuated position (for example, FIGS. 4A-D and 9A-D) to an actuated position (for example, FIGS. 5A-D and 10A-D), for example, with the thumb of the hand that holds the housing 1, due to which the reset spring 9 becomes tensioned. During the movement of the actuation member 8 from the unactuated position to the actuated position, first the third coupling 1c, 8c becomes coupled, so that the drive spring is operably connected between the housing 1 and the driving member 4. The dose selection member 2 is then unable to rotate with respect to the housing 1. If the actuation member 8 is pressed further in the distal direction to the actuated position, the first coupling 4a, 7a becomes coupled, so that the rotation member 7 cannot rotate with respect to the driving member 4. Additional movement of the actuation member 8 to its actuated position causes the second coupling 2b, 4b to become uncoupled, so that the torque of the drive spring 5 is directed via the fourth coupling 7a, 11f in the housing 1, so that the drive spring 5 cannot yet relax. Only when the fourth coupling 7a, 11f becomes uncoupled, with the achievement of the actuated position of the actuation member 8, can the drive spring 5, which rests at its first end at housing 1, release the spring energy stored in it in the form of rotational energy to the rotation member 7 via the driving member 4, so that the driving member 4 rotates in the second direction of rotation. In this case, the rotation member 7 also rotates in the second direction of rotation, so that the driven member 3 likewise is rotated in the second direction of rotation and screws in the distal direction on the internal thread 1a, so that the piston 6e is moved in the distal direction and the product contained in the product container 6 is discharged. Because of the non-rotatable connection between the driving member 4 and the dose display member 10, the dose display element 10 is screwed back to its zero dose position at the same time. When the zero dose stop 10e strikes the zero dose counterstop 11b, the selected dose has been completely discharged, and due to the stop of the zero dose discharge 10e at the zero dose counterstop 11b, the dose display element 10 becomes stopped in its rotation, so that the driving member 4 also is stopped in its rotation in the second direction of rotation. This situation is shown, for example, in FIGS. 5A-5D. When the user releases the actuation member 8, the reset spring 9 returns the actuation member 8 to its unactuated position, and the first coupling 4a, 7a, the second coupling 2b, 4b, the third coupling 1c, 8c, and the fourth coupling 7a, 11f are returned to their starting positions. By turning the dose selection member 2 in the first direction of rotation, one can now again select a dose to be discharged, which can once more be discharged by actuation of the actuation member 8, and so forth. When an amount of product is contained in the product container 6 that is less than the maximum dose that can be discharged with the device, in this case less than 80 IU, the dose limiter 13 strikes its end stop when the dose selection member 2 is rotated in the first direction of rotation, before the maximum dose stop 10d strikes the maximum dose counterstop 11c. Because of this, the user of the device is prevented from injecting less product than was selected.

What is claimed is:

1. A drive and dosing device for an injection device for discharge of a liquid product, the drive and dosing device comprising:
   a housing;
   a dose selection member, which can be rotated relative to the housing for a selection of a product dose to be discharged;
   a driven member accommodated in the housing;
   a driving member, which can be rotated relative to the housing, and during the product discharge is coupled to the driven member so that a rotation of the driving member causes the driven member to be moved in a distal direction relative to the housing; and a pretensioned drive spring, which is connected by an elastically deformable segment, between the dose selection member and the driving member during the selection of the product dose, wherein the dose selection member is coupled non-rotatably to the driving member via a coupling during the selection of the product dose, such that a rotation of the driving member relative to the dose selection member is prevented, and the coupling is uncoupled during the product discharge such that the driving member can be rotated relative to the dose selection member by the pretensioned drive spring.

2. The drive and dosing device of claim 1, wherein the drive spring is pretensioned such that spring energy stored in the drive spring is sufficient to discharge completely the liquid product from a product container.

3. The drive and dosing device of claim 1, wherein the dose selection member is connected to the housing in an axially fixed manner.

4. The drive and dosing device of claim 1, wherein during the selection of the product dose, the dose selection member and the driving member are rotatable relative to the driven member and/or the housing in a first direction of rotation to increase the product dose to be discharged, and in a second direction of rotation to reduce the product dose to be discharged.

5. The drive and dosing device of claim 1, further comprising a second coupling between the driving member and the driven member, where the second coupling is uncoupled during the selection of the product dose and allows the driving member to be rotated relative to the driven member, and is coupled during the product discharge.

6. The drive and dosing device of claim 1, further comprising a rotation member operably connected between the driving member and the driven member.

7. The drive and dosing device of claim 6, further comprising a second coupling between the driving member and the driven member, where the second coupling is uncoupled during the selection of the product dose and allows the driving member to be rotated relative to the driven member, and is coupled during the product discharge, and where the second coupling comprises a first coupling structure arranged on the driving member and a second coupling structure arranged on the rotation member.

8. The drive and dosing device of claim 6, wherein the rotation member is in a threaded engagement with a thread of the driven member and the driven member is in an engagement with a guide of the drive and dosing device that is affixed to the housing such that a rotation of the rotation member causes a movement of the driven member in the distal direction.

9. The drive and dosing device of claim 6, wherein a thread that is affixed to the housing is in a threaded engagement with a thread of the driven member and the driven member is in engagement with a guide of the rotation member such that a rotation of the rotation member causes a screwing motion of the driven member in the distal direction.

10. The drive and dosing device of claim 1, wherein a rotation of the driving member relative to the housing and/or the dose selection member causes the driven member to be moved in the distal direction relative to the housing.

11. The drive and dosing device of claim 1, further comprising an actuation member arranged at a proximal end of the drive and dosing device, wherein the actuation member is movable from an unactuated position, which the actuation member takes during the selection of the product dose to be discharged, to an actuated position, which the actuation member takes during the product discharge.

12. The drive and dosing device of claim 11, further comprising a reset spring, wherein the reset spring is tensed when the actuation member is moved from the unactuated position to the actuated position, and the tensed reset spring moves the actuation member from the actuated position to the unactuated position.

13. The drive and dosing device of claim 1, further comprising a second coupling between the dose selection member and the housing, where the second coupling is uncoupled during the selection of the product dose, whereby the dose selection member can be rotated relative to the housing, and is coupled during the product discharge, whereby the dose selection member cannot rotate relative to the housing.

14. The drive and dosing device of claim 13, wherein the second coupling is between a coupling structure of an actuation member and a coupling structure of the housing, wherein the actuation member and the dose selection member are non-rotatably coupled during the selection of the product dose and during the product discharge.

15. The drive and dosing device of claim 1, further comprising a dose display element comprising a dose scale on an outer circumference, wherein the display element is connected non-rotatably to the driving member such that the dose display element follows rotary movements of the driving member, and wherein the housing comprises an indicator device through which a scale value of the dose scale corresponding to a selected dose can be read.

16. The drive and dosing device of claim 1, wherein the drive spring is accommodated in an actuation member and couples to the actuation member such that the drive spring is supported indirectly at the dose selection member and/or the housing.

17. The drive and dosing device of claim 1, wherein the driving member comprises a proximal end and the actuation member comprises a contact surface, wherein the proximal end and the contact surface cooperate to reduce friction between the actuation member and the driving member when the driving member rotates relative to the actuation member during the product discharge.

18. The drive and dosing device of claim 17, wherein the proximal end of the driving member tapers towards the contact surface, and wherein a gap is defined between the proximal end and the contact surface when the actuation member is in the unactuated position, and wherein the proximal end fits closely to the contact surface when the actuation member is in the actuated position.

19. The drive and dosing device of claim 2, wherein the drive spring is a torsion spring.

20. A drive and dosing device for an injection device for discharge of a liquid product, the drive and dosing device comprising:

a housing;

a dose selection member, which can be rotated relative to the housing for a selection of a product dose to be discharged;

a driven member accommodated in the housing;

a driving member, which can be rotated relative to the housing, and during the product discharge is coupled to the driven member so that a rotation of the driving member causes the driven member to be moved in a distal direction relative to the housing; and a pretensioned drive spring, which is connected, via a first segment of the drive spring and a second segment of the drive spring, between the dose selection member and the driving member during the selection of the product dose, wherein the first segment of the drive spring and the second segment of the drive spring are separated by an elastically deformable third segment, wherein the dose selection member is coupled non-rotatably to the driving member via a coupling during the selection of the product dose, such that a rotation of the driving member relative to the dose selection member is prevented, and the coupling is uncoupled during the product discharge such that the driving member can be rotated relative to the dose selection member by the pretensioned drive spring, and wherein the pretensioned drive spring is pretensioned such that potential energy stored in the drive spring is sufficient to discharge completely the liquid product from a product container when the potential energy is released to the driving member.

21. A drive and dosing device for an injection device for discharge of a liquid product, the drive and dosing device comprising:
a housing;
a dose selection member, which can be rotated relative to the housing for a selection of a product dose to be discharged;
a driven member accommodated in the housing;
a driving member, which can be rotated relative to the housing, and during the product discharge is coupled to the driven member so that a rotation of the driving member causes the driven member to be moved in a distal direction relative to the housing;
a pretensioned drive spring, which is connected by an elastically deformable segment, between the dose selection member and the driving member during the selection of the product dose, where the dose selection member is coupled non-rotatably to the driving member in a coupling during the selection of the product dose, such that a rotation of the driving member relative to the dose selection member is prevented, and the coupling is uncoupled during the product discharge such that the driving member can be rotated relative to the dose selection member by the pretensioned drive spring, wherein the pretensioned drive spring is pretensioned such that potential energy stored in the drive spring is sufficient to discharge completely the liquid product from a product container when the potential energy is released to the driving member.

22. The drive and dosing device of claim 21, wherein during the selection of the product dose, the dose selection member and the driving member are rotatable relative to the driven member and/or the housing in a first direction of rotation to increase the product dose to be discharged, and in a second direction of rotation to reduce the product dose to be discharged.

23. The drive and dosing device of claim 21, further comprising a second coupling between the driving member and the driven member, where the second coupling is uncoupled during the selection of the product dose and allows the driving member to be rotated relative to the driven member, and is coupled during the product discharge.

24. The drive and dosing device of claim 21, further comprising a second coupling between the dose selection member and the housing, where the second coupling is uncoupled during the selection of the product dose, whereby the dose selection member can be rotated relative to the housing, and is coupled during the product discharge, whereby the dose selection member cannot rotate relative to the housing.

* * * * *